United States Patent
Muffoletto

(10) Patent No.: US 11,083,470 B2
(45) Date of Patent: Aug. 10, 2021

(54) EXPANDABLE REAMER CUTTING HEAD

(71) Applicant: VIANT AS&O HOLDINGS, LLC, Foxborough, MA (US)

(72) Inventor: Mark T. Muffoletto, Darien Center, NY (US)

(73) Assignee: Viant AS&O Holdings LLC, Foxborough, MA (US)

( * ) Notice: Subject to any disclaimer, the term of this patent is extended or adjusted under 35 U.S.C. 154(b) by 0 days.

(21) Appl. No.: 16/294,606

(22) Filed: Mar. 6, 2019

(65) Prior Publication Data
US 2019/0274694 A1    Sep. 12, 2019

Related U.S. Application Data

(60) Provisional application No. 62/639,053, filed on Mar. 6, 2018.

(51) Int. Cl.
*A61B 17/16*    (2006.01)
*A61B 17/17*    (2006.01)

(52) U.S. Cl.
CPC ........ *A61B 17/1617* (2013.01); *A61B 17/164* (2013.01); *A61B 17/17* (2013.01)

(58) Field of Classification Search
CPC ... A61B 17/16; A61B 17/164; A61B 17/1617; A61B 17/17
See application file for complete search history.

(56) References Cited

U.S. PATENT DOCUMENTS

| 2,385,999 | A | 10/1945 | McCallion |
|---|---|---|---|
| 6,224,604 | B1 | 5/2001 | Loubert |
| 6,383,188 | B2 | 5/2002 | Kuslich et al. |
| 2006/0264958 | A1 | 11/2006 | Ezzedine |
| 2009/0306689 | A1 | 12/2009 | Welty et al. |
| 2012/0070244 | A1 | 3/2012 | Stern |
| 2015/0150589 | A1* | 6/2015 | Yamanouchi ........ A61B 17/221 606/159 |

(Continued)

FOREIGN PATENT DOCUMENTS

| WO | 2002062226 A1 | 8/2002 |
|---|---|---|
| WO | 2009148805 A1 | 12/2009 |

OTHER PUBLICATIONS

International Search Report and Written Opinion relating to PCT/US2019/21006, dated May 9, 2019.

*Primary Examiner* — Christopher J Beccia
(74) *Attorney, Agent, or Firm* — Steven J. Grossman; Grossman, Tucker, Perreault & Pfleger, PLLC

(57) ABSTRACT

A medical device comprising a rotatable cutter head having a center longitudinal rotation axis; the rotatable cutter head comprising a mandrel and a plurality of elongated cutters disposed on the mandrel; each of the elongated cutters rotatable about a cutter rotation axis, respectively, wherein rotation of each of the elongated cutters about the cutter rotation axis changes a cutting diameter of the rotatable cutter head; each cutter rotation axis having a length which simultaneously extends both longitudinally along the center longitudinal rotation axis and circumferentially around the center longitudinal rotation axis; and each cutter rotation axis parallel with a first imaginary plane, respectively, which is at an angle with a second imaginary plane which is parallel to the center longitudinal axis, respectively.

36 Claims, 15 Drawing Sheets

(56) References Cited

U.S. PATENT DOCUMENTS

| | | |
|---|---|---|
| 2015/0257769 A1 | 9/2015 | Papenfuss |
| 2015/0282817 A1 | 10/2015 | Osman et al. |
| 2017/0245869 A1* | 8/2017 | Mirochinik ........ A61B 17/1764 |
| 2018/0042618 A1* | 2/2018 | Victor ................ A61B 17/1617 |

* cited by examiner

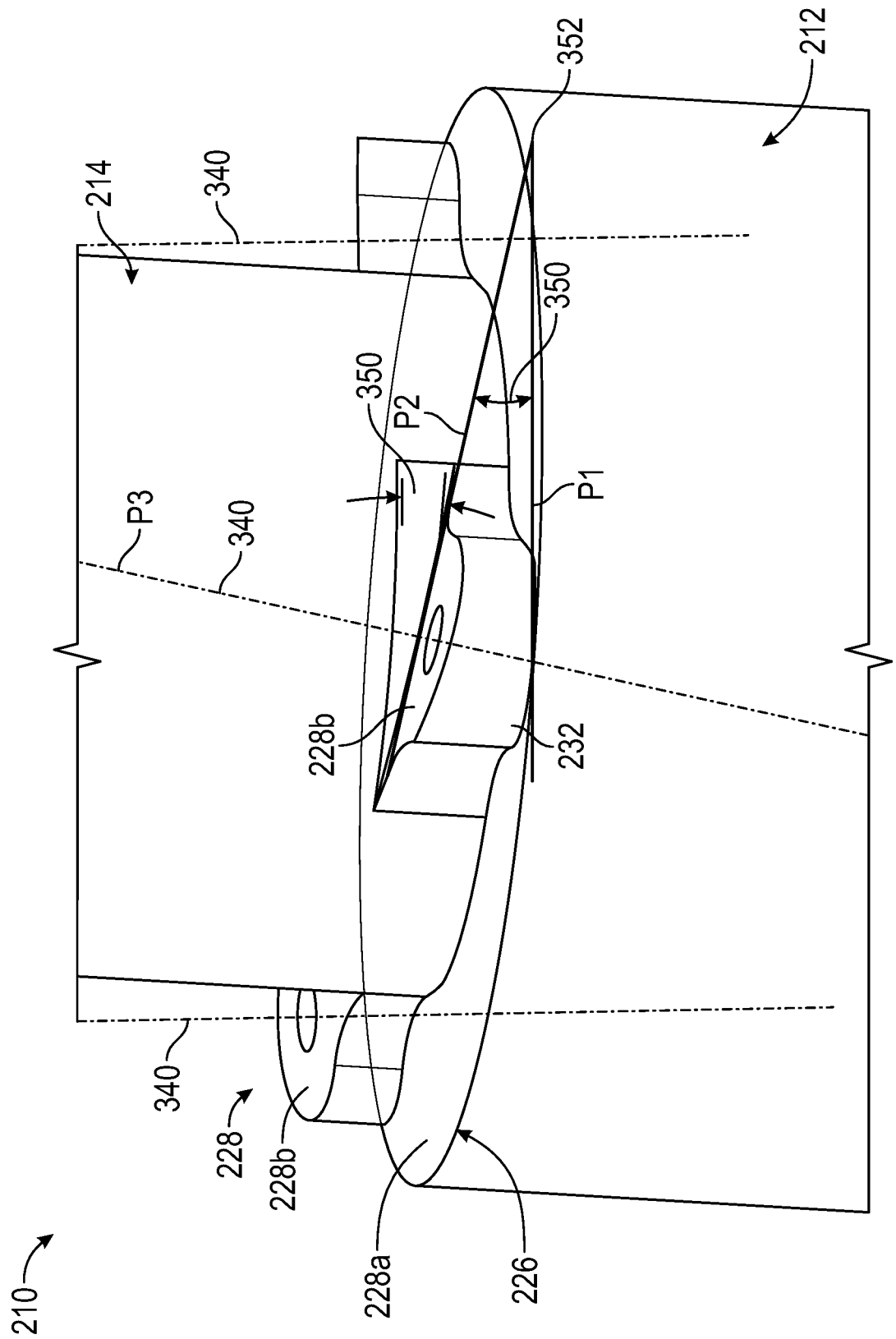

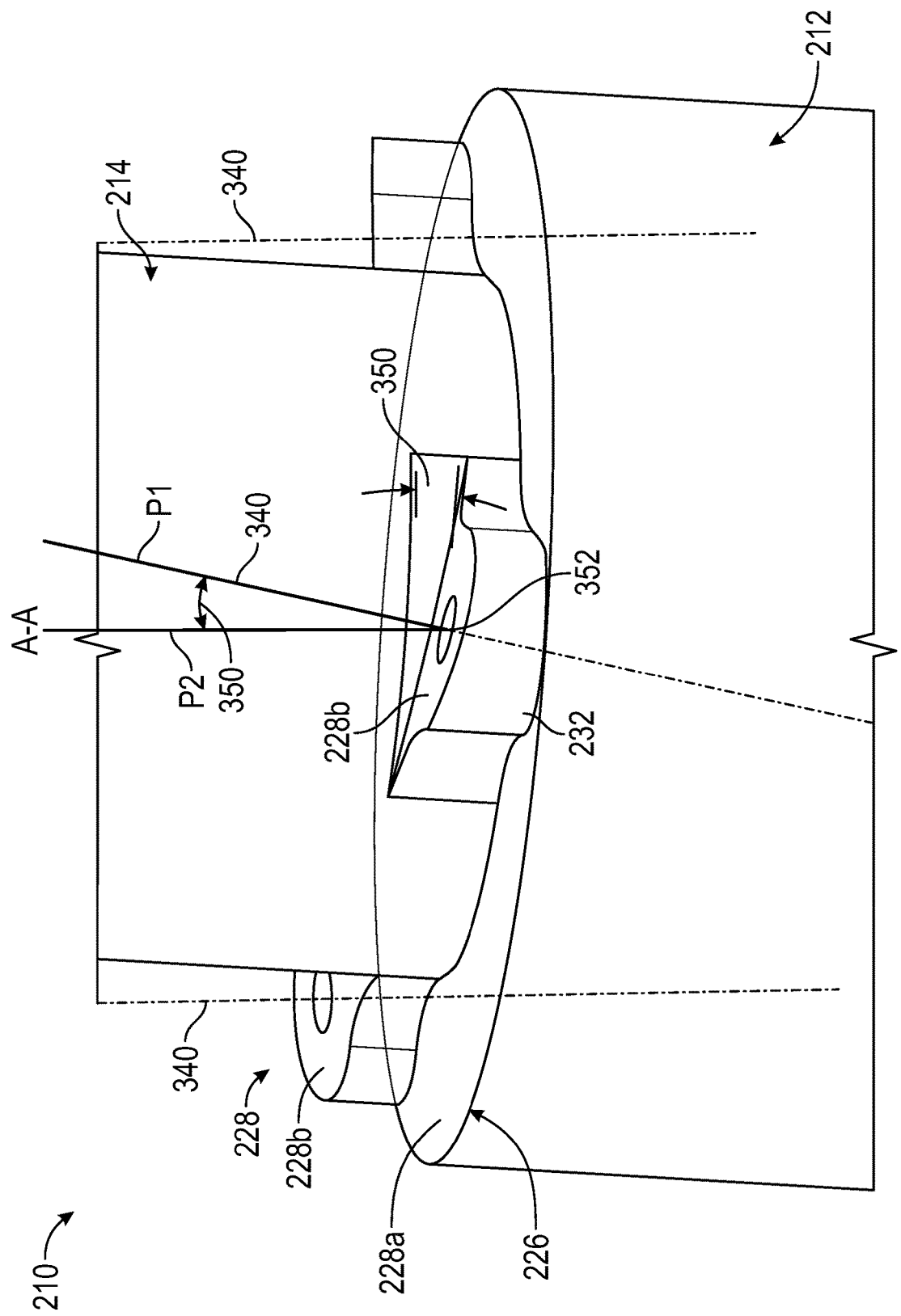

EXPANDABLE REAMER CUTTING HEAD

CROSS-REFERENCE TO RELATED APPLICATIONS

This application claims the benefit of U.S. provisional patent application Ser. No. 62/639,053, filed Mar. 6, 2018, which is incorporated herein by reference in its entirety.

FIELD

The present disclosure relates generally to medical devices. More particularly, the present disclosure relates to cutting heads and use thereof in orthopedic surgical procedures to excise tissue such as bone and, even more particularly, expandable intramedullary reamer cutting heads therefor.

BACKGROUND

The following description is provided for background understanding of the art. None of the information provided or references cited is admitted to be prior art.

U.S. Patent Publication No. 2015/0282817, entitled "Expandable Reamer and Method of Use, which is hereby incorporated by reference in its entirety, describes a spinal reamer which has blades that fold away to provide a minimally invasive method of removing disc material. This prior art utilizes a mechanism to open blades about an axis which is perpendicular to a longitudinal axis of the device.

U.S. Pat. No. 6,383,188, entitled "Expandable Reamer," which is also hereby incorporated by reference in its entirety, functions very similar to the above. A vertebral disc reamer with hinged blades that operate in a planar direction in a either open or closed state, with the blades hinging about an axis which is perpendicular to a longitudinal axis of the device.

U.S. Pat. No. 6,224,604, entitled "Expandable Orthopedic Drill For Vertebral Interbody Fusion Techniques," which is also hereby incorporated by reference in its entirety, describes a spinal reamer that has fixed cutters of semicylindrical shape that are tied to a fixed central hub using linkages. The final proximal linkage is attached to a threaded tube that fits concentrically over the main shaft that is fixed to the central hub. As the threaded tube is moved proximally, the linkages force the cutters to move out radially, with translational motion, effectively increasing the cutting diameter.

U.S. Pat. No. 2,385,999, entitled "Expanding Reamer," which is also, hereby incorporated by reference in its entirety, discloses a reamer that uses opposing thread pitches to slide wedges in and out along a central axle. Between these "inner" and "outer" wedges are blades that have fixed cutting edges. The blades free float inside the device and are captured by the wedges. As the wedges transverse the threads of the central axle, they move the in or out radially with translational motion.

SUMMARY

Conventional orthopedic procedures may be understood to rely upon a plurality of reamers during a procedure, such as part of a kit, to perform intramedullary (IM) reaming. In this respect, conventional procedures can be advanced by replacing the status quo, i.e., typically a surgical tray supporting various reamers and component parts, with a single expandable reamer. To this end, the time required to perform an operation may be reduced at least insofar as the surgeon would be able to adjust the reaming diameter with the reamer still installed on a guidewire. Furthermore, to the extent that such an expandable reamer is employed within a disposable system, the number of sterilization cycles and components would also be minimized.

In one aspect, the present disclosure reduces the number of surgical tools required to perform intramedullary (IM) reaming. In this regard, replacing a tray of reamers with a single expandable reamer reduces the time required to perform an operation by allowing the surgeon to adjust the reaming diameter him/her self with the reamer still installed on a guidewire. Furthermore, if/when used in conjunction with a disposable reamer system, the disclosed expandable reamer may reduce the number of components run through a hospital cleaning and sterilization process per surgery.

As such, in illustrative embodiments, an object of the present disclosure entails replacing a tray of surgical reamers with a single adjustable diameter reamer. Effectively reducing the amount of tools required in a single procedure, as well as decreasing the time required to perform a surgery, by reducing the number of tool changes required to achieve a final diameter. In this respect, the foregoing is accomplished inasmuch as an adjustable reamer head is provided in accord with all existing orthopedic surgical systems, which require a physical tool change to adjust sizes.

In certain embodiments, a medical device is provided comprising, a rotatable cutter head having a center longitudinal rotation axis; the rotatable cutter head comprising a mandrel and a plurality of elongated cutters disposed on the mandrel; each of the elongated cutters rotatable about a cutter rotation axis, respectively, wherein rotation of each of the elongated cutters about the cutter rotation axis changes a cutting diameter of the rotatable cutter head; each cutter rotation axis having a length which simultaneously extends both longitudinally along the center longitudinal rotation axis and circumferentially around the center longitudinal rotation axis; and each cutter rotation axis parallel with a first imaginary plane, respectively, which is at an angle with a second imaginary plane which is parallel to the center longitudinal axis, respectively.

In certain embodiments, a medical device is provided comprising, a rotatable cutter head having a center longitudinal rotation axis; the rotatable cutter head comprising a mandrel and a plurality of elongated cutters disposed on the mandrel; each of the elongated cutters rotatable about a cutter rotation axis, respectively, wherein rotation of each of the elongated cutters about the cutter rotation axis changes a cutting diameter of the rotatable cutter head; each cutter rotation axis having a length which simultaneously extends both longitudinally along the center longitudinal rotation axis and circumferentially around the center longitudinal rotation axis; each elongated cutter comprising a cutter blade having a proximal end and a distal end; and the cutter rotation axis of each elongated cutter is spaced at a radial distance from the longitudinal axis which changes 1.5 mm or less from the proximal end to the distal end of the cutter blade.

In certain embodiments, a medical device is provided comprising, a rotatable cutter head having a center longitudinal rotation axis; the rotatable cutter head comprising a mandrel and a plurality of elongated cutters disposed on the mandrel; each of the elongated cutters rotatable about a cutter rotation axis, respectively, wherein rotation of each of the elongated cutters about the cutter rotation axis changes a cutting diameter of the rotatable cutter head; each cutter rotation axis having a length which simultaneously extends both longitudinally along the center longitudinal rotation axis and circumferentially around the center longitudinal rotation axis; each the cutter rotation axis is spaced at a radial distance from the longitudinal axis; and each cutter rotation axis extends circumferentially around the center longitudinal rotation axis in a range of 1% to 15% of a full rotation around the center longitudinal rotation axis.

FIGURES

The foregoing summary and following description are illustrative with respect to the present disclosure, and as such are not intended to be in any way limiting. In addition to the illustrative aspects, embodiments, and features described, further aspects, embodiments, and features will become apparent by reference to the following drawings and as further detailed herein, wherein:

FIG. 1F is a close-up perspective view of the cylindrical mandrel of the end effector (expandable cutting head) of FIG. 1A;

FIG. 1G is another close-up perspective view of the cylindrical mandrel of the end effector (expandable cutting head) of FIG. 1A;

DETAILED DESCRIPTION

Figure 1A:
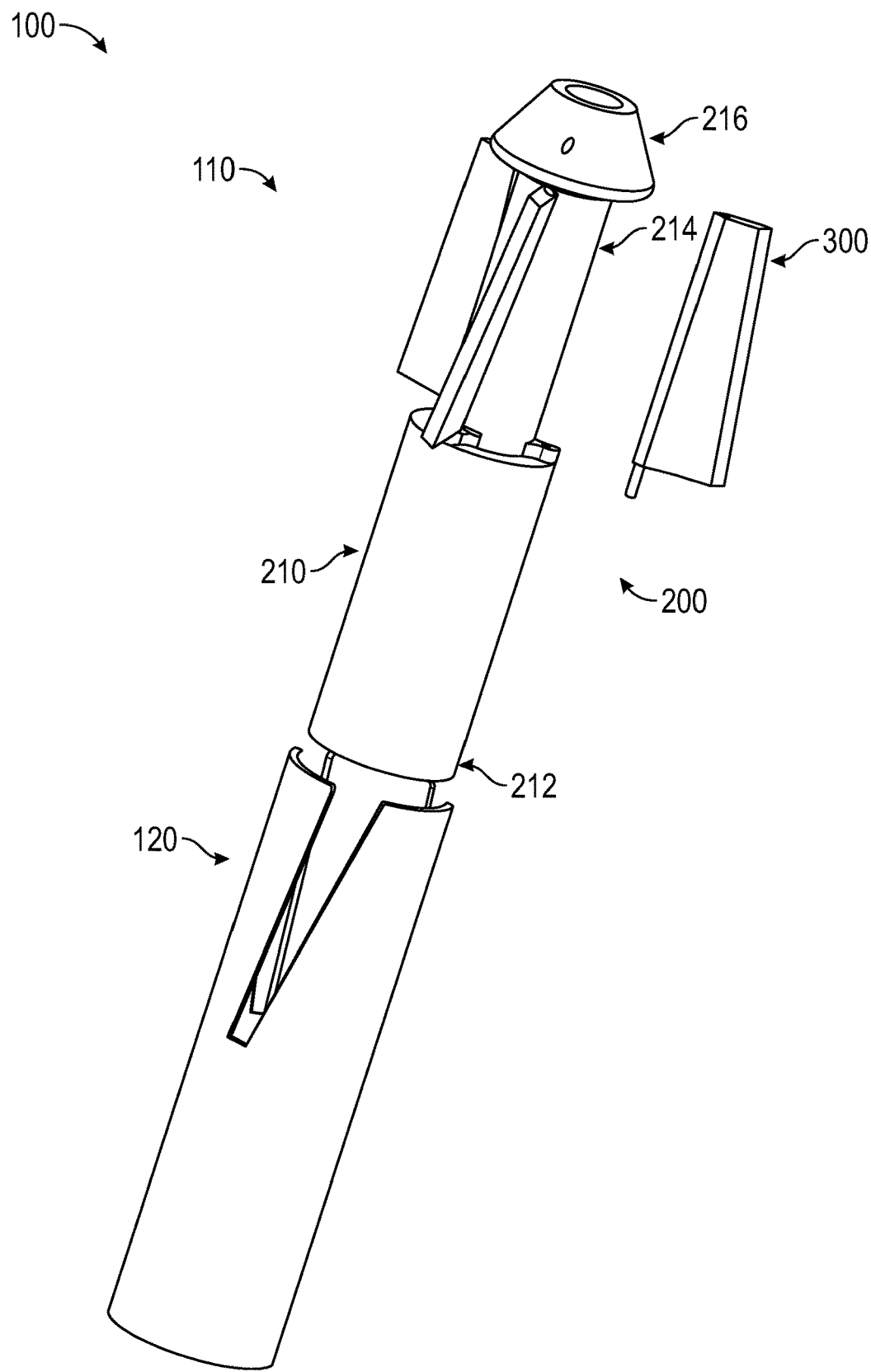
FIG. 1A is an illustrative exploded perspective view of an end effector of a medical device, particularly an expandable intramedullary (IM) reamer cutting head, of the present disclosure.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

In the following detailed description, reference is made to the accompanying drawings, which form a part thereof. In the drawings, similar symbols typically identify similar components, unless context dictates otherwise. The illustrative embodiments described in the detailed description and drawings can be arranged, substituted, combined, separated, and designed in a wide variety of different configurations, all of which are explicitly contemplated herein.

As used herein, the terms "device" or "instrument" refer to medical component(s) typically employed in an orthopedic procedure. In illustrative embodiments, the medical devices and instruments of the present disclosure include a proximal end and a distal end, where typically, for example, the distal end of the device or instrument is the functional region that, in illustrative embodiments, contacts the area of the patient being operated on, e.g., the distal end is typically not the device region contacted by the clinician or surgeon. The expandable IM reamer cutting heads, in this regard, would be located on, at or about the distal end of a medical device. The proximal end, on the other hand, for example, is the structural region that, in illustrative embodiments, is contacted by the clinician or surgeon. In other words, the proximal end or region of a medical device typically does not come into contact with a patient's body.

Referring now to the figures, there is shown a cutting end effector 110, particularly of a hand-manipulated or machine-manipulated medical device 100. The cutting end effector 110, as shown, is more particularly an expandable cutting head, and even more particularly an expandable intramedullary (IM) reamer cutting head.

Figure 1B:
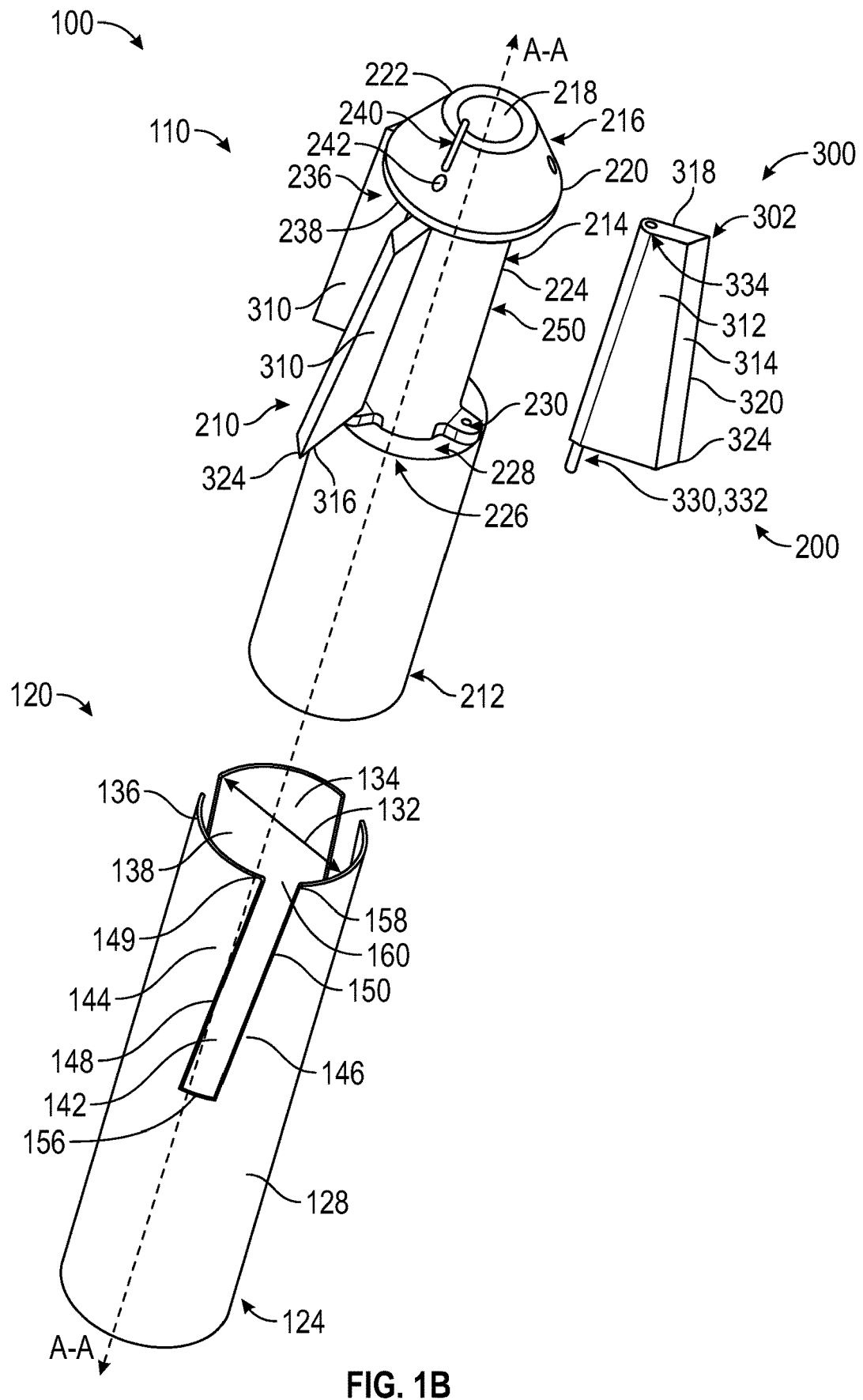
FIG. 1B is another illustrative exploded perspective view of the end effector (expandable cutting head) of FIG. 1A.

Referring particularly to FIG. 1A and FIG. 1B, the cutting end effector (cutting head) 110 comprises an elongated outer cutter guide 120, which may also be referred to as a drum. Elongated outer cutter guide 120 particularly comprises a circular tubular body 124, which extends along a center longitudinal axis A-A, which corresponds to the center longitudinal axis of rotation of the expandable (reamer) cutting head.

Figure 1C:
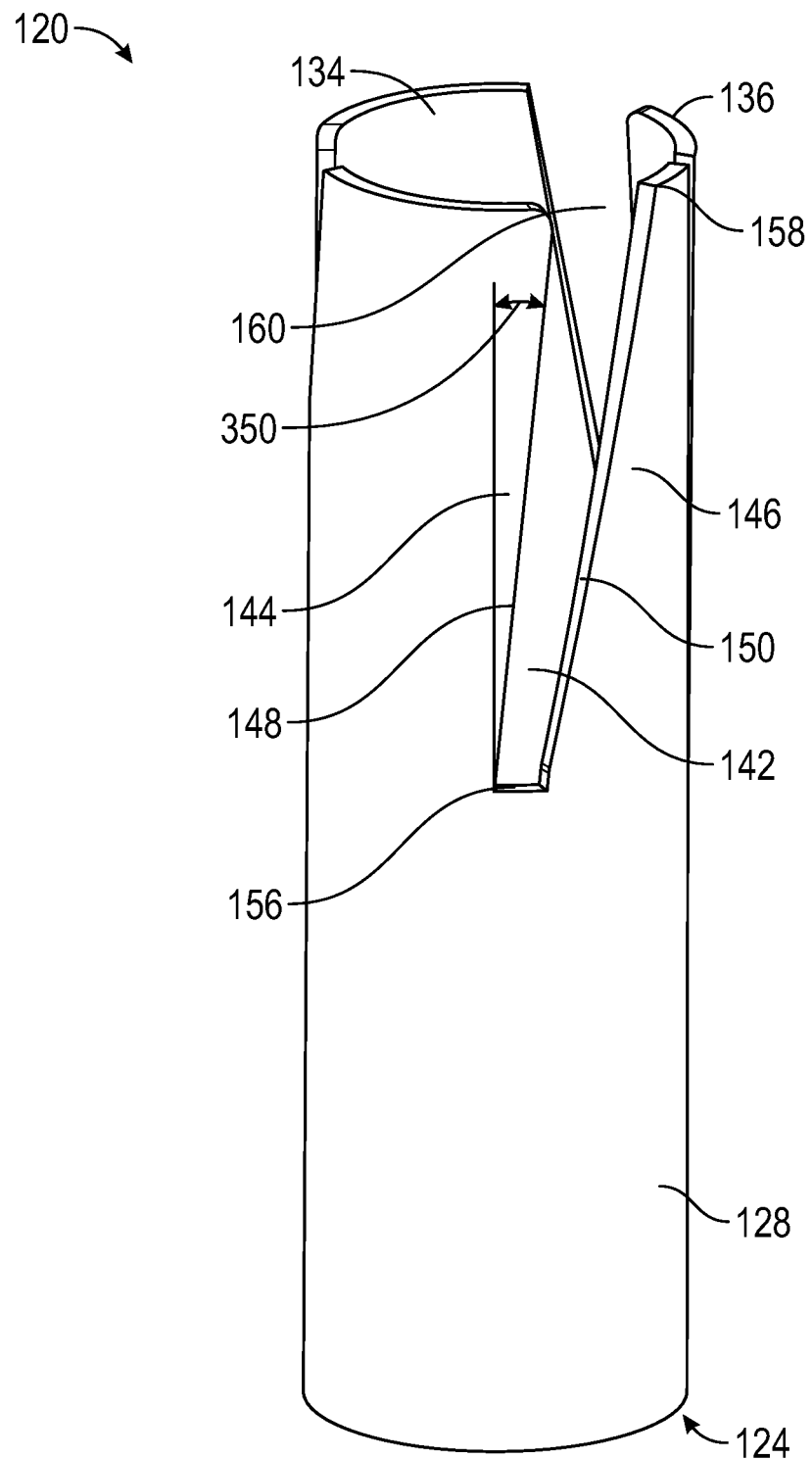
FIG. 1C is a perspective view of the elongated cutter guide of the end effector (expandable cutting head) of FIG. 1A.

Referring also to FIG. 1C, circular tubular body 124 comprises a cylindrical side wall 128, which defines an inner diameter 132 of an inner circular (cylindrical) passage 134. As shown, the inner diameter 132 is preferably constant along the longitudinal length of the tubular body 124. Cylindrical side wall 128 terminates at a distal end 136, which defines a distal end opening 138.

Cylindrical tubular body 124 includes a plurality of elongated apertures 142, which may be referred to as cutter guide/blade slots or distal open ended slotted apertures, formed in and defined by the sidewall 128. As shown, the opposing sections 144, 146 of sidewall 128 define the longitudinal length of each elongated aperture 142, with section 144 of sidewall 128 located at a trailing side of elongated cutter 300 and section 146 of sidewall 128 located at a leading side of elongated cutter 300. As shown, section 144 of sidewall 128 terminates in am aperture trailing edge 148 which defines aperture 142 at the trailing side of elongated cutter 300, while section 146 of sidewall 128 terminates in an aperture leading edge 150 which defines aperture 142 at the leading side of elongated cutter 300. Leading edge 150 of the aperture 142 has a helical profile. By way of example, the helical profile may have a pitch of 139 mm, and extend about 0.10 revolutions (10%) around the circumference (i.e. 36 degrees) of the elongated outer cutter guide 120.

Proximal end 156 of each elongated aperture 142 is also defined by sidewall 128, which defines a proximal end width of each elongated aperture 142 between opposing longitudinal edges 148, 150. The distal end 158 of each elongated aperture 142 has a distal end width also defined between opposing longitudinal edges 148, 150. The distal end 158 is defined by the distal end opening 160 between opposing longitudinal edges 148, 150. As shown, that distal end opening 138 of passage 134 and the distal end opening 160 of elongated apertures 142 lie in the same plane transverse (perpendicular) to the center longitudinal axis A-A, and are adjacent and in contact with one another.

As shown, the cutting end effector (expandable cutting head) 110 further comprises a cutter assembly 200. Cutter assembly 200 comprises a cylindrical mandrel 210, which may also be referred to as a hub, which comprises a unitary (monolithic) body having a proximal cylindrical section 212, a distal cylindrical section 214 and a conical distal end (cap) section 216. A cylindrical center passage 218, which may be referred to as a cannula, extends completely through the cylindrical mandrel 210, having a center disposed on the center longitudinal axis A-A. The cylindrical center passage 218 may be used for installation and passage of a guidewire there through during use of the device 100. The mandrel 210 may be mounted in a chuck (i.e. a clamp used to hold a rotating tool with radial symmetry, especially a cylinder) in a known manner.

As shown, the proximal cylindrical section 212 has an outer diameter which substantially corresponds to the inner diameter 132 of circular tubular body 124, sized slightly smaller than the inner diameter 132 of circular tubular body 124, such that when assembled, the circular tubular body 124 is movable (e.g. slidable) proximally/distally over the cylindrical mandrel 210.

The conical distal end section 216 has an outer diameter which nearly corresponds to the outer diameter of the circular tubular body 124, sized substantially the same, such that when assembled, the proximal end 220 of the distal end cap 220 may contact the distal end 136 of the circular tubular body 124, without being small enough to extend into the inner passage 134. While the conical distal end section 216 has (conical) face 222 is shown not to include cutter blades for simplicity, the distal end section 216 may include cutter blades 223 as shown in FIG. 1H. The distal end section 216 as shown in FIG. 1H is more fully disclosed and described in U.S. Patent Publication No. 2017/0231643, entitled "Cutting Heads For Intramedullary Reamers", which is hereby incorporated by reference in its entirety.

As shown, the distal cylindrical section 214 has an outer diameter smaller than both the outer diameter of the proximal end section 212 and the proximal end 220 of the distal end section 216. As a result of the reduced diameter of distal cylindrical section 214 in relation to the proximal end section 212 and the proximal end 220 of the distal end section 216, an annular recess 250 is formed, an inner side of which is defined in part by the cylindrical surface 224 of distal cylindrical section 214.

Annular recess 250 is further defined by a proximal annular face 228 formed by a distal shoulder region 226 of proximal cylindrical section 212, as well as a distal annular face 238 formed by a proximal shoulder region 236 of distal end section 216 at the proximal end 220.

Cutter assembly 200 further comprises a plurality of substantially identical elongated cutters 300 (identical, e.g. except for manufacturing tolerance). While three cutters 300 are shown, the number of cutters 300 may typically range from two cutters 300 to six cutters 300, with the circumferential space between cutter blades 302 of cutters 300 providing helical flutes for removal of cut bone and other tissue.

Figure 1D:
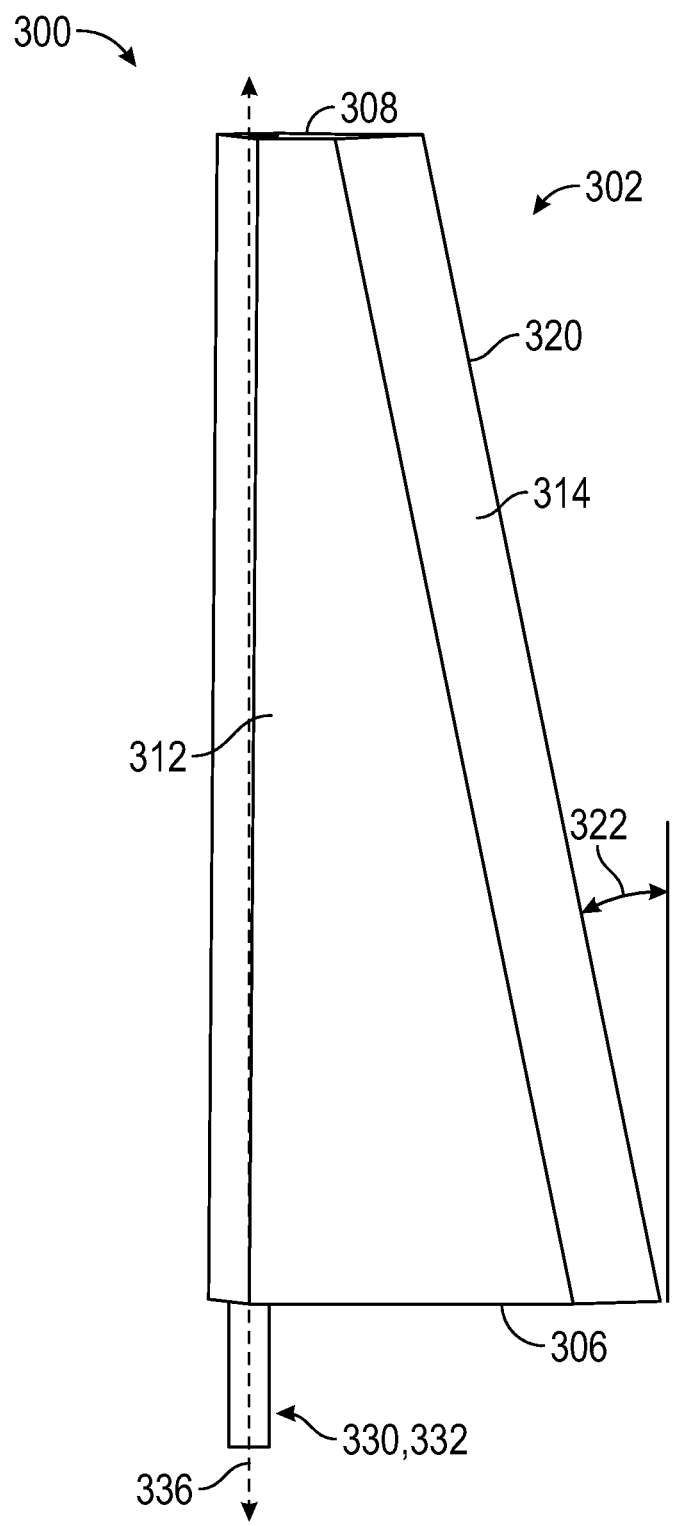
FIG. 1D is a side view of an elongated cutter of the end effector (expandable cutting head) of FIG. 1A.

As best shown by FIG. 1D, cutters 300 each comprise a body having an elongated, planar cutter blade 302 and at least one mounting/connector member 330 to mount/connect the cutter 300 to the cylindrical mandrel 210.

Cutter blade 302 comprises a proximal end 306, a distal end 308, a leading face 310 and a trailing face 312. Distal end 308 includes a distal end tissue cutting edge 318. Trailing face 312 includes a bevel 314 which narrows the thickness of the cutter blade 302 along its longitudinal length to a tissue cutting edge 320, which extends longitudinally (proximally/distally). While a single bevel 314 (i.e. only on the trailing face 312) is shown the cutter blade 302 may include a double bevel, in which both the leading face 310 and the trailing face 312 both include a bevel, or only the leading face 312 may include a bevel. As shown, the bevel angle is 45 degrees, however any suitable bevel angle may be used. The bevel angle may also be referred to as a relief angle.

Cutter blade 302 also tapers from the proximal end 306 to the distal end 308 at a taper angle 322, which is shown to be 20 degrees, however any suitable taper angle may be used. As shown, the width of the cutter blade 302 tapers uniformly at a constant taper angle 322 from the proximal end 306 to the distal end 308, however the cutter blade 302 may have a plurality of different taper angles 322 along the longitudinal length of the cutter blade 302.

The at least one mounting/connector member 330 may comprise a proximal mounting/connector member 332 and a distal mounting/connector member 334.

Proximal mounting/connector member 332 of the elongated cutter 300 connects with a mounting/connector member 230 disposed on the proximal cylindrical section 212 of the cylindrical mandrel 210, as well as on the distal cylindrical section 214 of the cylindrical mandrel 210.

The proximal mounting/connector member 332 of the elongated cutter 300 comprises a cylindrical axle (which may also be referred to as a pivot pin), while the mounting connector/member 230 on the proximal cylindrical section 212 of the cylindrical mandrel 210 comprises a cylindrical blind bore configured to receive the cylindrical axle 332, which has a center longitudinal axis 336 extending along a length of the cylindrical axle 332. As shown, the cylindrical blind bore 230 of the mounting/connector member 230 configured to receive the cylindrical axle 332 of the elongated cutter 300 may be defined by a portion 232 of the cylindrical mandrel 210, shown as a mounting tab, disposed on the proximal cylindrical section 212 of the cylindrical mandrel 210, as well as on the distal cylindrical section 214 of the cylindrical mandrel 210. As shown, the portion 232 of the cylindrical mandrel 210 containing bore 230 may be connected to, and thus part of, the proximal cylindrical section 212 and/or the distal cylindrical section 214 of the cylindrical mandrel 210.

The cylindrical axle 332 has a smaller diameter than the cylindrical blind bore 230 such that the cylindrical axle 332 is rotatable within the cylindrical blind bore 230. As will become more apparent below, the cylindrical axle 332 provides an axle for rotation of the elongated cutter 300/cutter blade 302 about an elongated cutter/cutter blade rotation axis 340, which is at an angle (i.e. non-parallel or not parallel) with the center longitudinal axis A-A of the cylindrical mandrel 210 and the cutter guide 120. Of course, in other embodiments, the location of the cylindrical axle 332 and the cylindrical blind bore 230 may be reversed.

Distal mounting/connector member 334 of the elongated cutter 300 connects with a mounting connector/member 240 of the distal end section 216 of the cylindrical mandrel 210. The distal mounting/connector member 334 of the elongated cutter 300 comprise a cylindrical blind bore, while the mounting connector/member 240 of the distal end section 216 of the cylindrical mandrel 210 comprises a cylindrical axle 240 (which may also be referred to as a pivot pin). The cylindrical blind bore 334 is configured to receive the cylindrical axle 240.

The cylindrical blind bore 334 has a larger diameter than the cylindrical axle 240 such that the cylindrical blind bore 334, and hence the elongated cutter 300, is rotatable about the cylindrical axle 240, particularly on the same axis as the cylindrical axle 332 within the cylindrical blind bore 230. In such regard, cylindrical axle 332 also forms part of the axle for rotation of the elongated cutter 300/cutter blade 302 about an elongated cutter/cutter blade rotation axis 340. Cylindrical axle 240 may be press fit into a through bore 242 formed in distal end section 216. Of course, in other embodiments, the location of the cylindrical axle 240 and the cylindrical blind bore 334 may be reversed.

In order to assemble cutter assembly 200, Proximal mounting/connector member (axle) 332 of the elongated cutter 300 may first be inserted the mounting connector/member (blind bore) 230 of the proximal cylindrical section 212 of the cylindrical mandrel 210 while tipped an angle relative to the elongated cutter/cutter blade rotation axis 340. The distal mounting/connector member (blind bore) 334 of the elongated cutter 300 may then be axially aligned with the through bore 242 of the distal end section 216. Thereafter, the mounting connector/member (axle) 240 may be inserted through through-bore 242 and into distal mounting/connector member (blind bore) 334 of the elongated cutter 300. The distal mounting/connector member (blind bore) 334 of the elongated cutter 300 has a larger diameter that the diameter of the through bore 242 of the distal end section 216 such that the mounting connector/member (axle) 240 may be press fit within through bore 242 of the distal end section 216, while still permitting the distal mounting/connector member (blind bore) 334 of the elongated cutter 300 to rotate about mounting connector/member (axle) 240 of the distal end section 216.

Figure 1E:
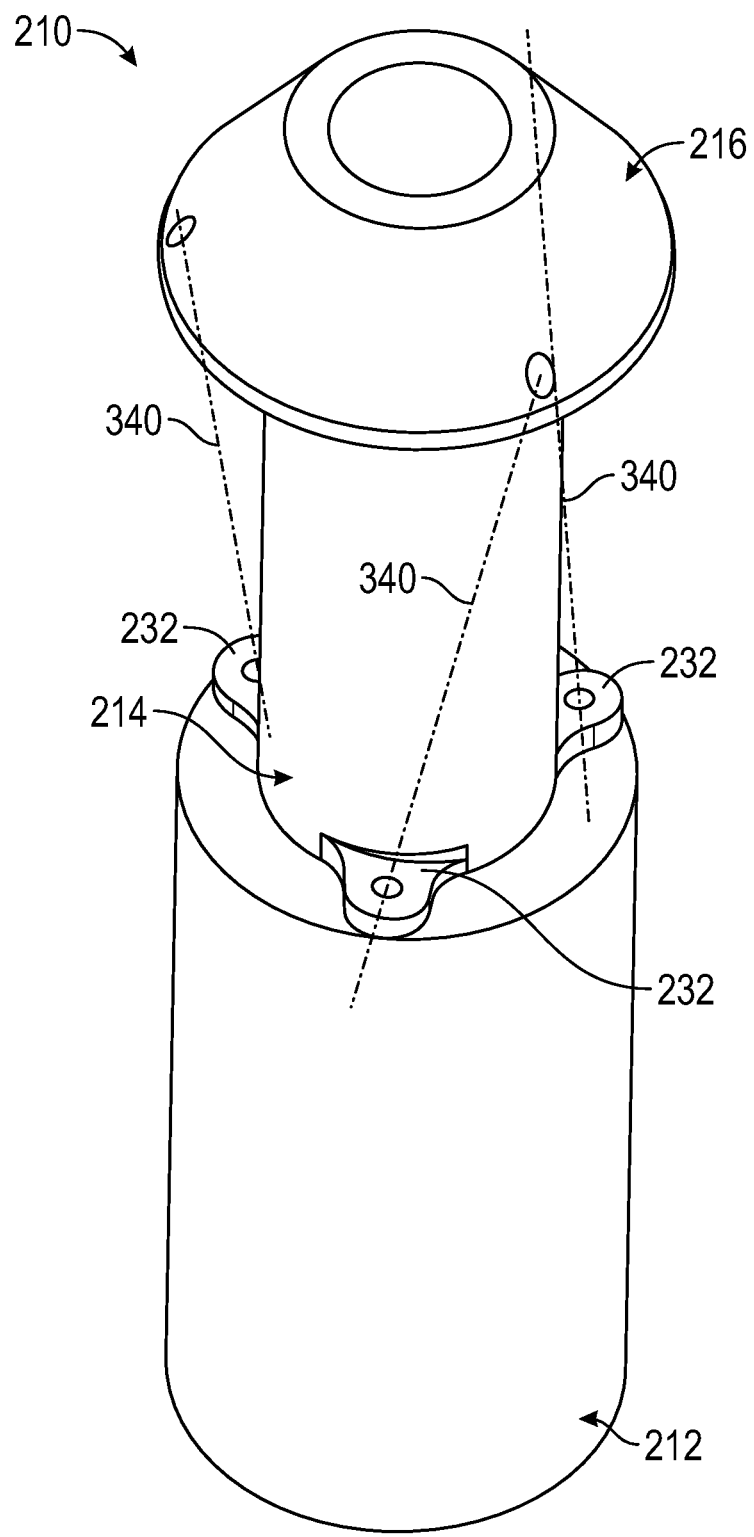
FIG. 1E is a perspective view of the cylindrical mandrel of the end effector (expandable cutting head) of FIG. 1A.
Figure 1H:
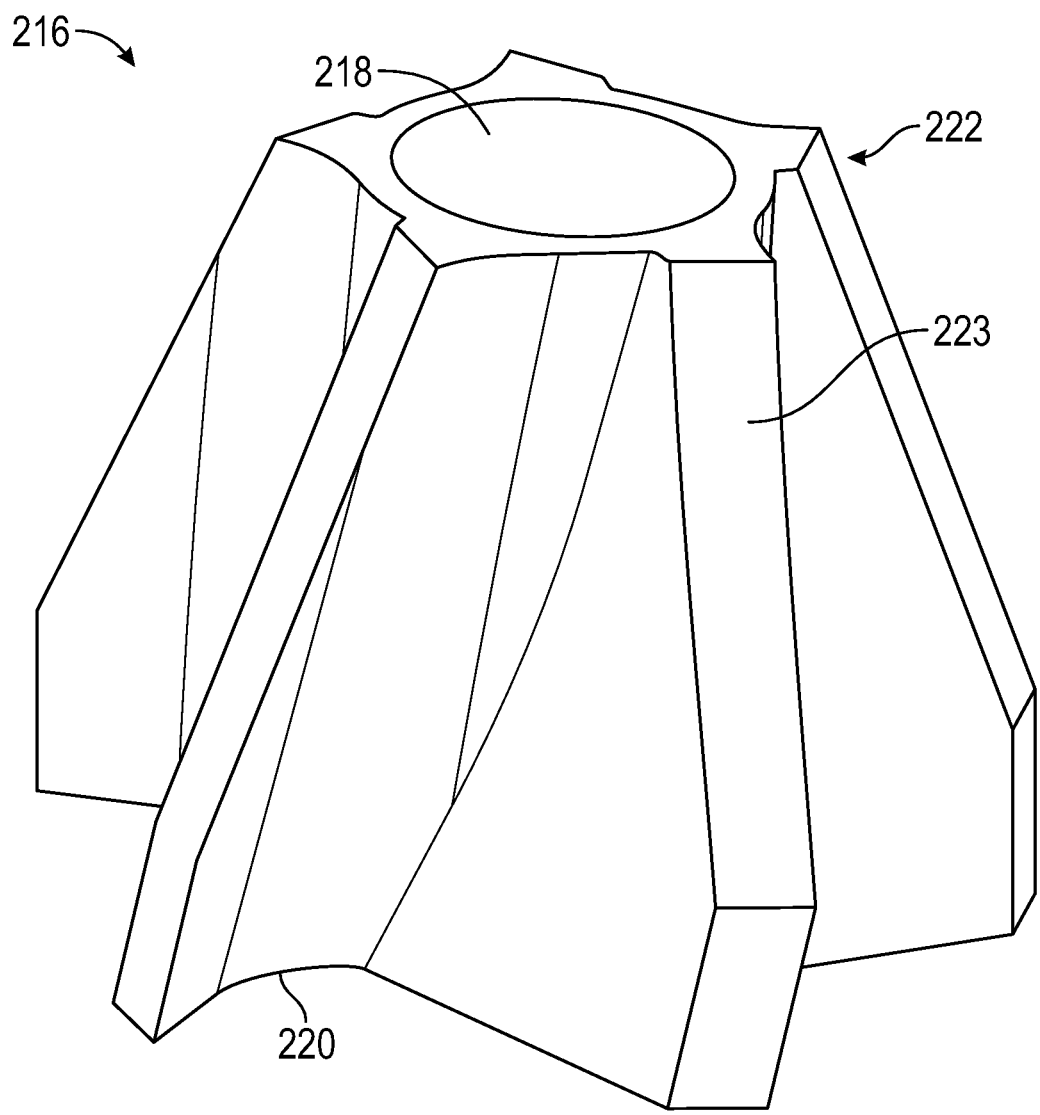
FIG. 1H is a perspective view of a distal end section of the cylindrical mandrel of the end effector (expandable cutting head) according to another embodiment of the present disclosure.

Referring now to FIGS. 1E and 1F, each elongated cutter 300/cutter blade 302 is rotatable about its own rotation axis 340 on axle 332, 340 (which may be provided by pivot pins) of the elongated cutter 300 rotates. As shown the annular face 228 of proximal cylindrical section includes a face segment 228a provided by the distal shoulder region 226 of proximal cylindrical section 212, as well as a face segment 228b provided by portion 232 of the cylindrical mandrel 210 disposed on the proximal cylindrical section 212 of the cylindrical mandrel 210, as well as on the distal cylindrical section 214 of the cylindrical mandrel 210.

Referring now to FIG. 1F, face segment 228a, provided by the distal shoulder region 226 of proximal cylindrical section 212, lies in an imaginary plane P1, which is normal (perpendicular) to the center longitudinal axis A-A. Face segment 228b lies in an imaginary plane P2, which is at an angle 350 (which may be referred to as the elongated cutter/cutter blade axle angle) with the imaginary plane P1, with the vertex 352 of the axle angle 350 at the intersection of the imaginary planes P1, P2. At the blade axle angle 350, the elongated cutter/cutter blade axle axis 340 lies in an imaginary plane P3 normal (perpendicular) to face segment 228b.

From a different geometry perspective, referring now to FIG. 1G, the center longitudinal axis A-A lies in an imaginary plane P2, which is parallel to the center longitudinal axis A-A. The elongated cutter/cutter blade axle axis 340 lies in an imaginary plane P1 which is at axle angle 350 with imaginary plane P2, with the vertex 352 of the axle angle 350 at the intersection of the imaginary planes P1, P2.

As shown best by FIGS. 1B and 1E, the elongated cutter/cutter blade axle axis 340 maintains a substantially constant radial distance (e.g. changes 1.5 mm or less, or more particularly changes 1 mm or less) from the center longitudinal axis A-A along a longitudinal length of the cutter blade 302 from the proximal end 306 to the distal end 308. Moreover, due to the angle 350 of the axle axis 340 for each elongated cutter 300/cutter blade 302, the axle axis 340 at the distal end 308 of the cutter blade 302 is circumferentially forward of the axle axis 340 at the proximal end 306 of the cutter blade 302 in the cutting direction, i.e. the counter-clockwise direction when the cutting end effector (expandable cutting head) 110 is viewed distally to proximally.

As shown, each of the cutting blades 300 are arranged equally spaced circumferentially within annular recess 250 relative to the cylindrical surface 224 of distal cylindrical section 214, as well as each other. Moreover, each of the cutting blades 300 are arranged equally radially distant from the center longitudinal axis A-A of the cylindrical mandrel 210 and the cutter guide 120.

Once the elongated cutters 300 are assembled to the cylindrical mandrel 210, the cutter assembly 200 may be inserted into the inner passage 134 of the tubular body 124 of the cutter guide 120, with at least a portion of each elongated cutter 300 occupying one of the elongated sidewall apertures 142, respectively (i.e. in a one-to-one relationship).

Referring to FIGS. 2A-2H, with use of medical device 100, the cutting end effector (expandable cutting head) 110 provides an expandable cutting diameter, particularly by rotating each of the elongated cutters 300/cutter blades 302 on their respective axles about their respective axle angles 350 when a position of the tubular body 124 of the cutter guide 120 is moved longitudinally, proximally or distally, along the longitudinal axis A-A. As shown in FIGS. 2A-2H, the cutter assembly 200 is shown to be rotated in a counter-clockwise cutting direction when the cutting end effector (expandable cutting head) 110 is viewed distally to proximally or, alternatively, rotated in a clockwise cutting direction when cutting end effector (expandable cutting head) 110 is viewed proximally to distally.

Figure 2A:
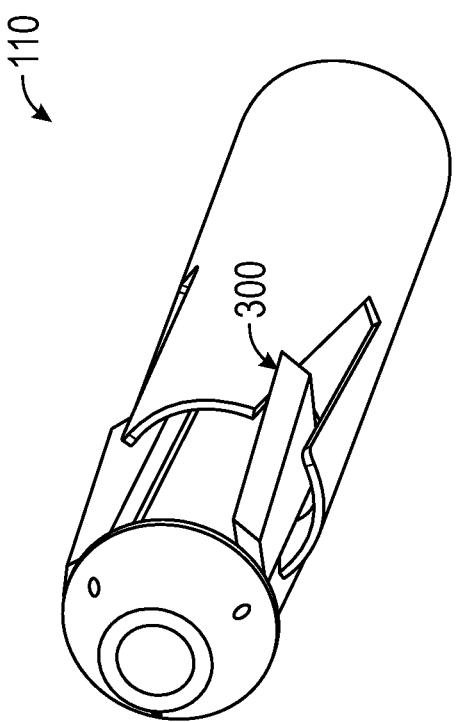
FIG. 2A is illustrative perspective view of the expandable cutting head of FIG. 1A, where the cutters are shown positioned to form a 9.5 mm reaming diameter.
Figure 2B:
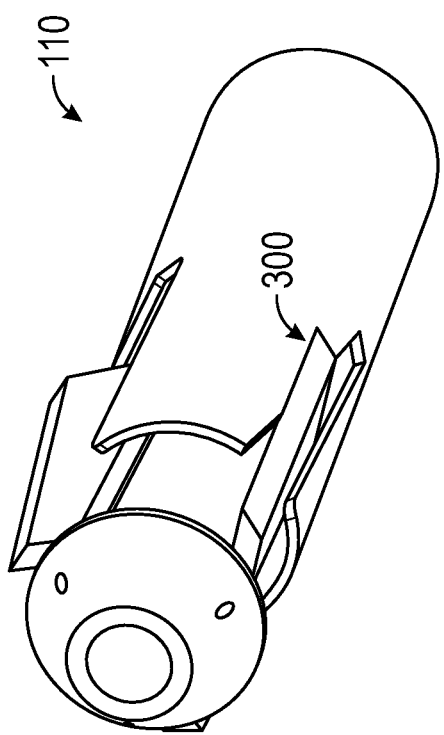
FIG. 2B is illustrative perspective view of the expandable cutting head of FIG. 1A, where the cutters are shown positioned to form a 10.5 mm reaming diameter.
Figure 2C:
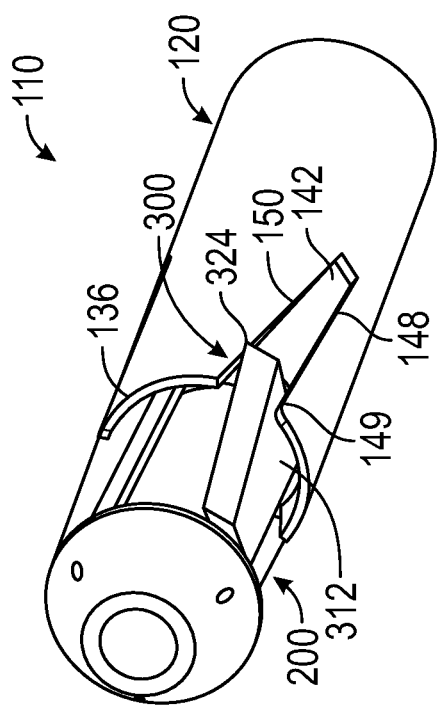
FIG. 2C is illustrative perspective view of the expandable cutting head of FIG. 1A, where the cutters are shown positioned to form a 11.5 mm reaming diameter.
Figure 2D:
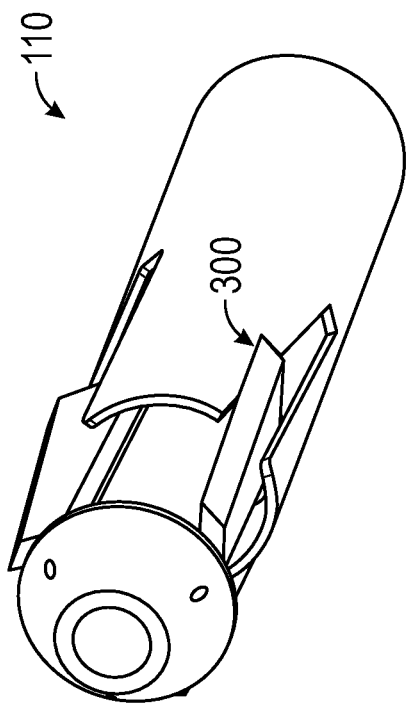
FIG. 2D is illustrative perspective view of the expandable cutting head of FIG. 1A, where the cutters are shown positioned to form a 12.5 mm reaming diameter.
Figure 2E:
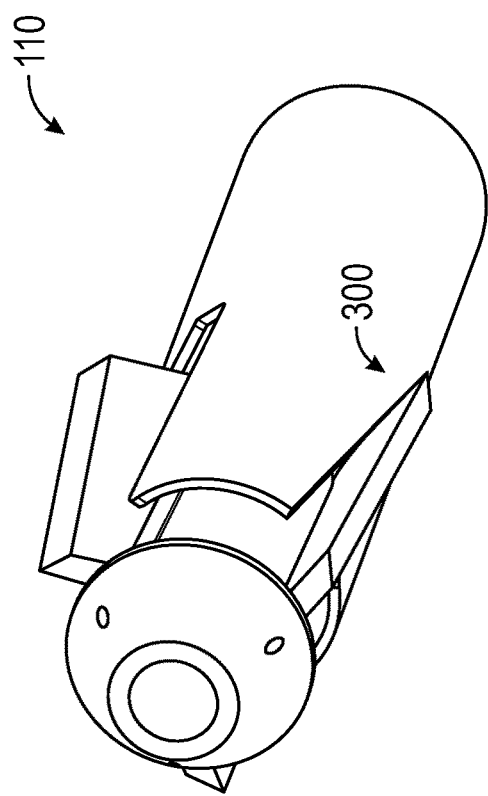
FIG. 2E is illustrative perspective view of the expandable cutting head of FIG. 1A, where the cutters are shown positioned to form a 13.5 mm reaming diameter.
Figure 2F:
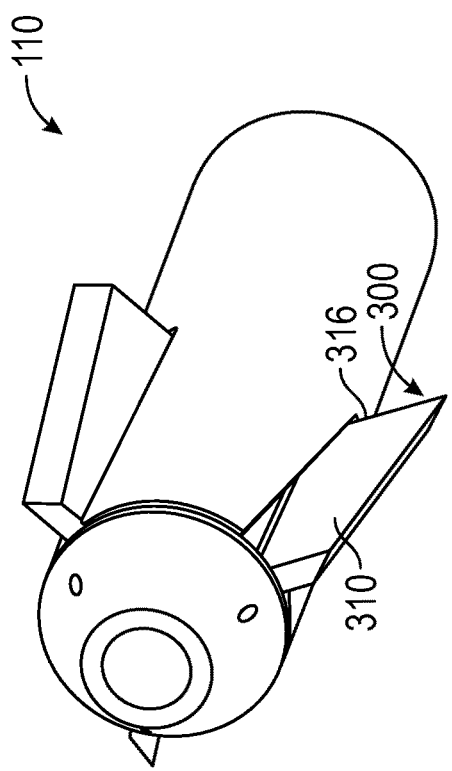
FIG. 2F is illustrative perspective view of the expandable cutting head of FIG. 1A, where the cutters are shown positioned to form a 14.5 mm reaming diameter.
Figure 2G:
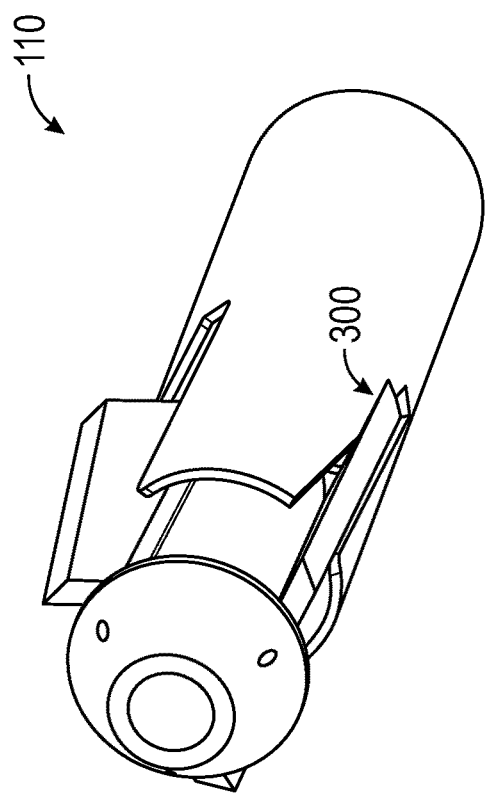
FIG. 2G is illustrative perspective view of the expandable cutting head of FIG. 1A, where the cutters are shown positioned to form a 15.5 mm reaming diameter.
Figure 2H:
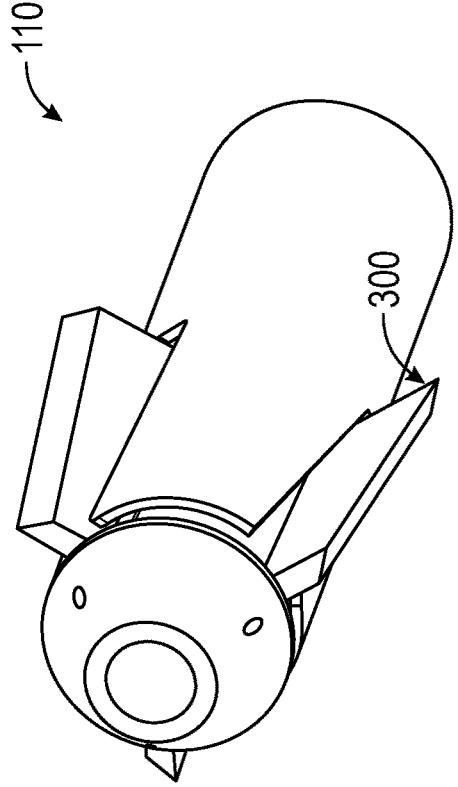
FIG. 2H is illustrative perspective view of the expandable cutting head of FIG. 1A, where the cutters are shown positioned to form a 16 mm reaming diameter.

More particularly, as shown in FIGS. 2A-2H, the leading edge 150 of the aperture 142, which again has a helical profile (which may be determined by the blade axle angle 350 and the taper angle 322), mechanically engages in contact with a leading engagement edge 316 (see FIG. 2H) of cutter blade 302. As shown in FIG. 2A, the elongated cutters 300/cutter blades 302 are in their most inward/retracted position, and the elongated cutter guide 120 is in its most proximal position relative to the cutter assembly 200. Thereafter, in FIGS. 2B-2H, the elongated cutter guide 120 is progressively moved distally along the longitudinal axis A-A, while the cutter assembly 200 is held stationary distally/proximally relative to the longitudinal axis A-A. Due to the contour of the leading edge 150 of the aperture 142, as the elongated cutter guide 120 is progressively moved distally along the longitudinal axis A-A, the resultant engagement contact with the leading engagement edge 316 of cutter blade 302 causes the elongated cutter 300/cutter blade 302 to rotate clockwise on rotation axis 340 (opposite the cutting direction) when viewed distally to proximally, thus increasing the cutting diameter. As shown in FIGS. 2A-2H, as the elongated cutter 300/cutter blade 302 increase in diameter, the portion of the leading engagement edge 316 of cutter blade 302 engaging with the leading edge 150 of the aperture 142 moves radially inward. As shown in FIG. 2H, the elongated cutters 300/cutter blades 302 are in their most outward/extended position, and the elongated cutter guide 120 is in its most distal position relative to the cutter assembly 200.

As shown, the contour of the trailing edge 148 of the aperture 142 is parallel with the trailing face 312 of the cutter blade 302 (i.e. the trailing edge 148 of the aperture 142 is at a same angle as the blade axle angle 350) to prevent the cutter blade 302 from opening further than the desired amount, in contrast to the helix cut of the leading edge 150 to force the cutter blade 302 to extend and retract with a linear change in blade diameter.

When it becomes desirable to collapse the elongated cutters 300/cutter blades 302 back to their most inward/retracted position, the elongated cutter guide 120 is progressively moved proximally along the longitudinal axis A-A, while the cutter assembly 200 is held stationary distally/proximally relative to the longitudinal axis A-A. Due to the contour of the trailing edge 148 of the aperture 142, as the elongated cutter guide 120 is progressively moved proximally along the longitudinal axis A-A, the resultant mechanical engagement contact of the distal end 149 of the trailing edge 148 of the aperture 142 with the trailing face 312 of the cutter blade 302 causes the elongated cutter 300/cutter blade 302 to rotate counter-clockwise on pivot axis 340 (same direction the cutting direction) when viewed distally to proximally, thus decreasing the cutting diameter.

In the foregoing manner, the cutting/reaming diameter of a cut passage within bone may be varied, without having to replace/change the cutting end effector (expandable cutting head) 110, thus saving time. As shown in FIG. 2A, the cutters 300 are shown positioned to form a 9.5 mm cutting/reaming diameter. In FIGS. 2B-2G, the cutters 300 are shown positioned to form a 10.5-15.5 mm cutting/reaming diameter, in 1 mm adjustments increments. However, it should be understood that the adjustment increment may include any distance, such as 0.5 mm. In FIG. 2H, the cutters 300 are shown positioned to form a 16 mm cutting/reaming diameter.

Figure 3A:
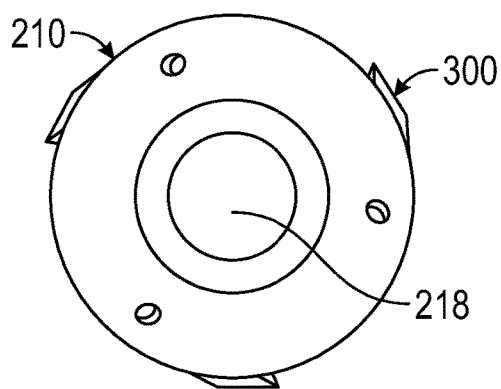
FIG. 3A is an illustrative distal end view of the end effector (expandable cutting head) with the cutters in a fully inward/retracted position.
Figure 3B:
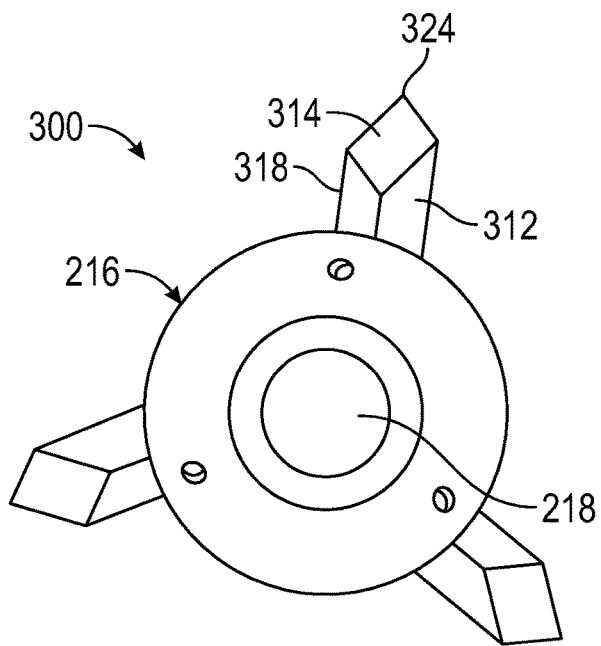
FIG. 3B is an illustrative distal end view of the end effector (expandable cutting head) with the cutters in a fully outward/extended position.

Referring to FIGS. 3A-3B, FIG. 3A is a distal end view of the end effector (expandable cutting head) 110 with the cutters 300 in a fully inward/retracted position, while FIG. 3B shows the cutters 300 in a fully outward/extended position.

Figure 4A:
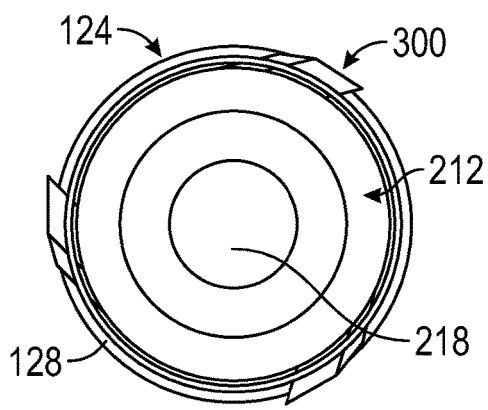
FIG. 4A is an illustrative proximal end view of the end effector (expandable cutting head) with the cutters in a fully inward/retracted position.
Figure 4B:
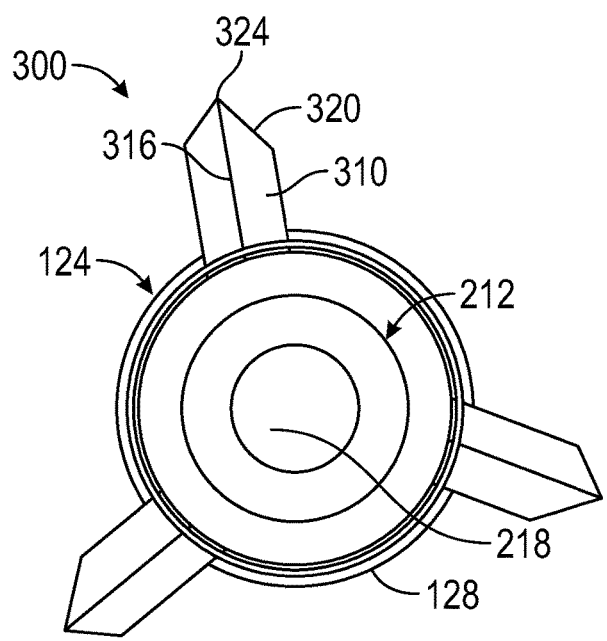
FIG. 4B is an illustrative proximal end view of the end effector (expandable cutting head) with the cutters in a fully outward/extended position.

Referring to FIGS. 4A-4B, FIG. 4A is a proximal end view of the end effector (expandable cutting head) 110 with the cutters 300 in a fully inward/retracted position, while FIG. 4B shows the cutters 300 in a fully outward/extended position.

Figure 5:
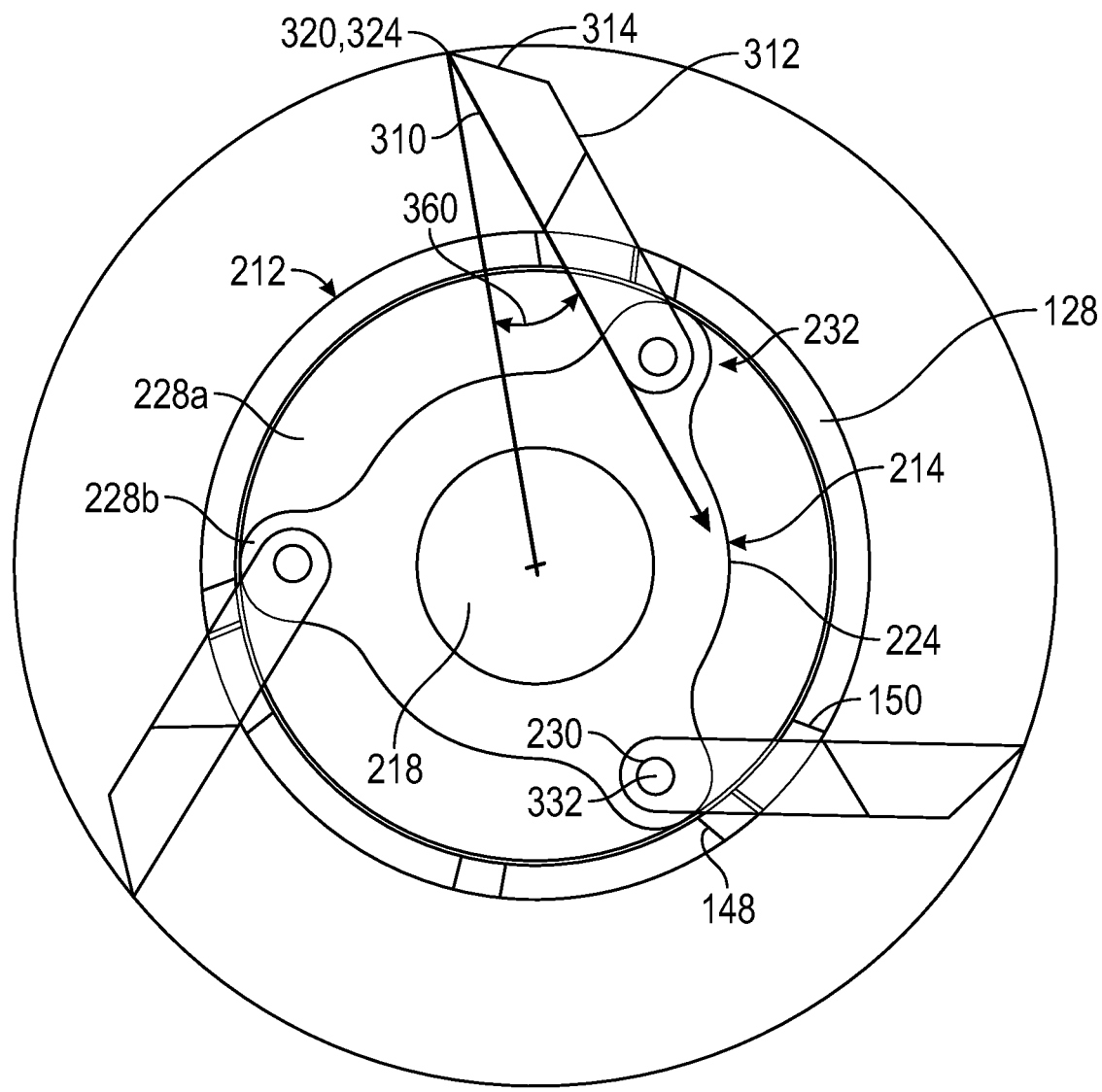
FIG. 5 is a cross-section of the end effector (expandable cutting head) taken normal (perpendicular) to the longitudinal axis A-A at the outermost cutting point of the cutting blade.

Referring to FIG. 1B and FIG. 5, due to the taper of cutter blade 302, the maximum cutting diameter of the cutter blade 302 occurs an outermost point 324 of the cutter blade 302 located at the distal end 308. As shown in FIG. 5, cutter blade 302 has a positive rake angle 360, which may be understood to be the angle created between two rays (sides), with a first ray/side connecting the center longitudinal axis A-A with the outermost point 324 of the cutter blade 302 (the tangent point of the cutting diameter, which is also the vertex of the rake angle 360), and a second ray/side connecting with the outermost point 324 of the cutter blade 302 and extending parallel with the leading face 310 of the cutter blade 302. As shown by Tables 1-5 below, the rake angle 360 remains positive at various blade axle angles 350 and blade taper angles 322 for each maximum cutting diameter between 9.5 mm and 16 mm.

TABLE 1

| Axle Angle 4 degrees, Blade Taper 8 degrees | |
|---|---|
| Cutting Diameter (mm) | Rake Angle (degrees) |
| 9.5 | 33.27 |
| 10 | 32.32 |
| 10.5 | 31.21 |
| 11 | 29.95 |
| 11.5 | 28.55 |
| 12 | 26.99 |
| 12.5 | 25.28 |
| 13 | 23.39 |
| 13.5 | 21.3 |
| 14 | 18.98 |
| 14.5 | 16.37 |
| 15 | 13.34 |
| 15.5 | 9.69 |
| 16 | 4.77 |

TABLE 2

Axle Angle 5 degrees, Blade Taper 8 degrees

| Cutting Diameter (mm) | Rake Angle (degrees) |
|---|---|
| 9.5 | 33.29 |
| 10 | 32.33 |
| 10.5 | 31.22 |
| 11 | 29.95 |
| 11.5 | 28.54 |
| 12 | 26.98 |
| 12.5 | 25.26 |
| 13 | 23.36 |
| 13.5 | 21.27 |
| 14 | 18.95 |
| 14.5 | 16.33 |
| 15 | 13.3 |
| 15.5 | 9.65 |
| 16 | 4.74 |

TABLE 3

Axle Angle 5 degrees, Blade Taper 10 degrees

| Cutting Diameter (mm) | Rake Angle (degrees) |
|---|---|
| 9.5 | 33.29 |
| 10 | 32.33 |
| 10.5 | 31.22 |
| 11 | 29.95 |
| 11.5 | 28.54 |
| 12 | 26.98 |
| 12.5 | 25.26 |
| 13 | 23.36 |
| 13.5 | 21.27 |
| 14 | 18.95 |
| 14.5 | 16.33 |
| 15 | 13.3 |
| 15.5 | 9.65 |
| 16 | 4.74 |

TABLE 4

Axle Angle 6 degrees, Blade Taper 8 degrees

| Cutting Diameter (mm) | Rake Angle (degrees) |
|---|---|
| 9.5 | 33.32 |
| 10 | 32.35 |
| 10.5 | 31.23 |
| 11 | 29.96 |
| 11.5 | 28.54 |
| 12 | 26.97 |
| 12.5 | 25.24 |
| 13 | 23.33 |
| 13.5 | 21.24 |
| 14 | 18.91 |
| 14.5 | 16.28 |
| 15 | 13.26 |
| 15.5 | 9.61 |
| 16 | 4.71 |

TABLE 5

Axle Angle 9 degrees, Blade Taper 12 degrees

| Cutting Diameter (mm) | Rake Angle (degrees) |
|---|---|
| 9.5 | 33.43 |
| 10 | 32.43 |
| 10.5 | 31.28 |
| 11 | 29.98 |
| 11.5 | 28.52 |
| 12 | 26.91 |
| 12.5 | 25.15 |
| 13 | 23.21 |
| 13.5 | 21.09 |
| 14 | 18.73 |
| 14.5 | 16.09 |
| 15 | 13.06 |
| 15.5 | 9.43 |
| 16 | 4.59 |

Thus, an exemplary cutting end effector (expandable cutting head) 110 according to the present disclosure may have a cutting diameter which may be in a range of 9.5 mm to 16 mm. The axle angle 350 may be in a range of 1 degree to 10 degrees, and more particularly 4 degrees to 9 degrees. As such, the cutter rotation axis 340 may extend circumferentially around the center longitudinal rotation axis A-A in a range of 1% to 15% of a full rotation around the center longitudinal rotation axis A-A.

The blade taper angle 322 may be in a range of 8 degrees to 12 degrees. The blade taper angle 322 is preferably larger than the corresponding axle angle 350, particularly to allow the rake angle 360 to remain positive over the range of cutting (reaming) diameters.

Thus, as disclosed, the cutting end effector (expandable cutting head) 110 of the present disclosure utilizes rotatable cutter blades which each are configured to each rotate on their own rotation axle which increases or decreases a cutting diameter of the cutting end effector (expandable cutting head) 110. More particularly, the expandable cutting head is an expandable reamer cutting head utilizes rotatable cutter blades which each are configured to each rotate on their own rotation axle which increases or decreases a reaming diameter of the expandable reamer cutting head 110. The rotation axle of each of the rotatable cutter blades is at an axle angle relative to a longitudinal axis of rotation of the expandable (reamer) cutting head, which rotation of the cutter blade about the axle angle increases or decreases a reaming diameter of the expandable (reamer) cutting head 110.

Referring now to FIGS. 6A-6D, the medical device 100/cutting end effector (expandable cutting head) 110 may include an anti-rotation mechanism 400 which inhibits the tubular body 124 of the elongated cutter guide 120 and cylindrical mandrel 210 of the cutter assembly 200 from rotating relative to one another. As shown the anti-rotation mechanism 400 may comprise an elongated enclosed aperture/slot 170 formed in the tubular body 124 of the elongated cutter guide 120 which extends parallel with the center longitudinal axis A-A, which is occupied by a cylindrical pin 260 of the cylindrical mandrel 210 which extends transverse to the center longitudinal axis A-A. As shown, the width of the elongated enclosed aperture/slot 170 corresponds to the diameter of the cylindrical pin 260, which inhibits the tubular body 124 of the elongated cutter guide 120 and cylindrical mandrel 210 of the cutter assembly 200 from rotating relative to one another.

Figure 6C:
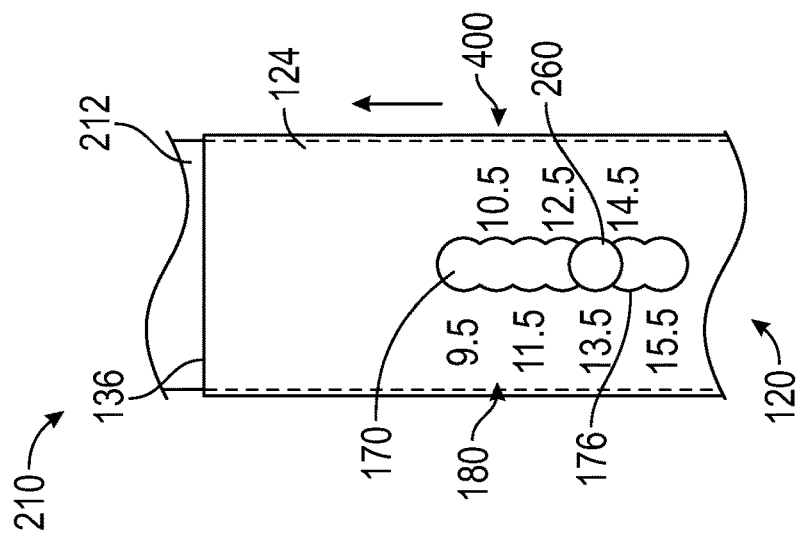
FIG. 6C shows another section side view of the elongated cutter guide and mandrel of FIG. 1A.
Figure 6B:
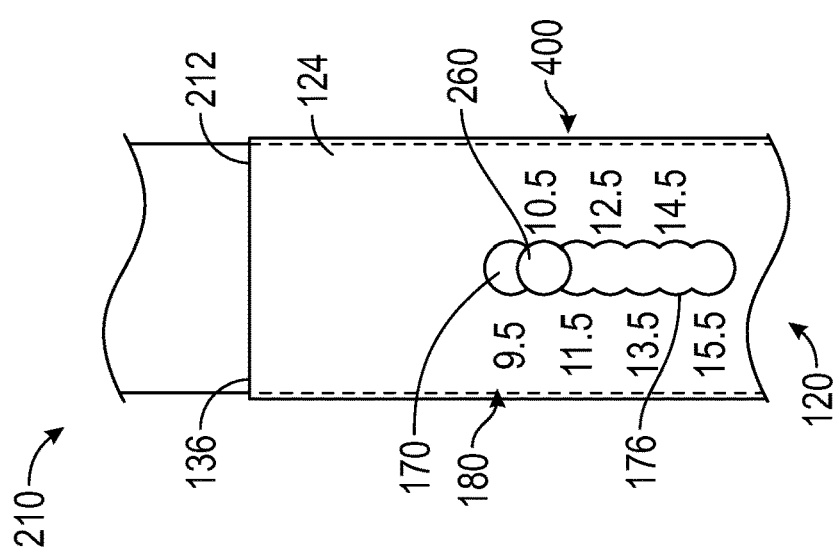
FIG. 6B shows a section side view of the elongated cutter guide and mandrel of FIG. 1A.
Figure 6A:
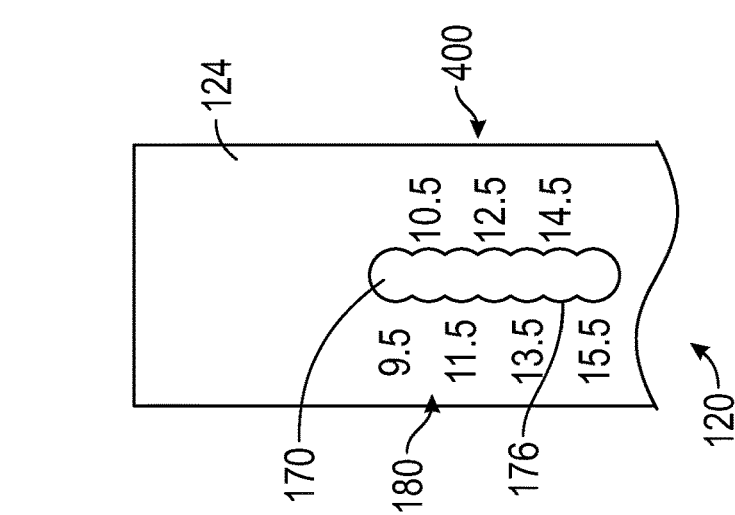
FIG. 6A shows a section side view of the elongated cutter guide of FIG. 1A.
Figure 6D:
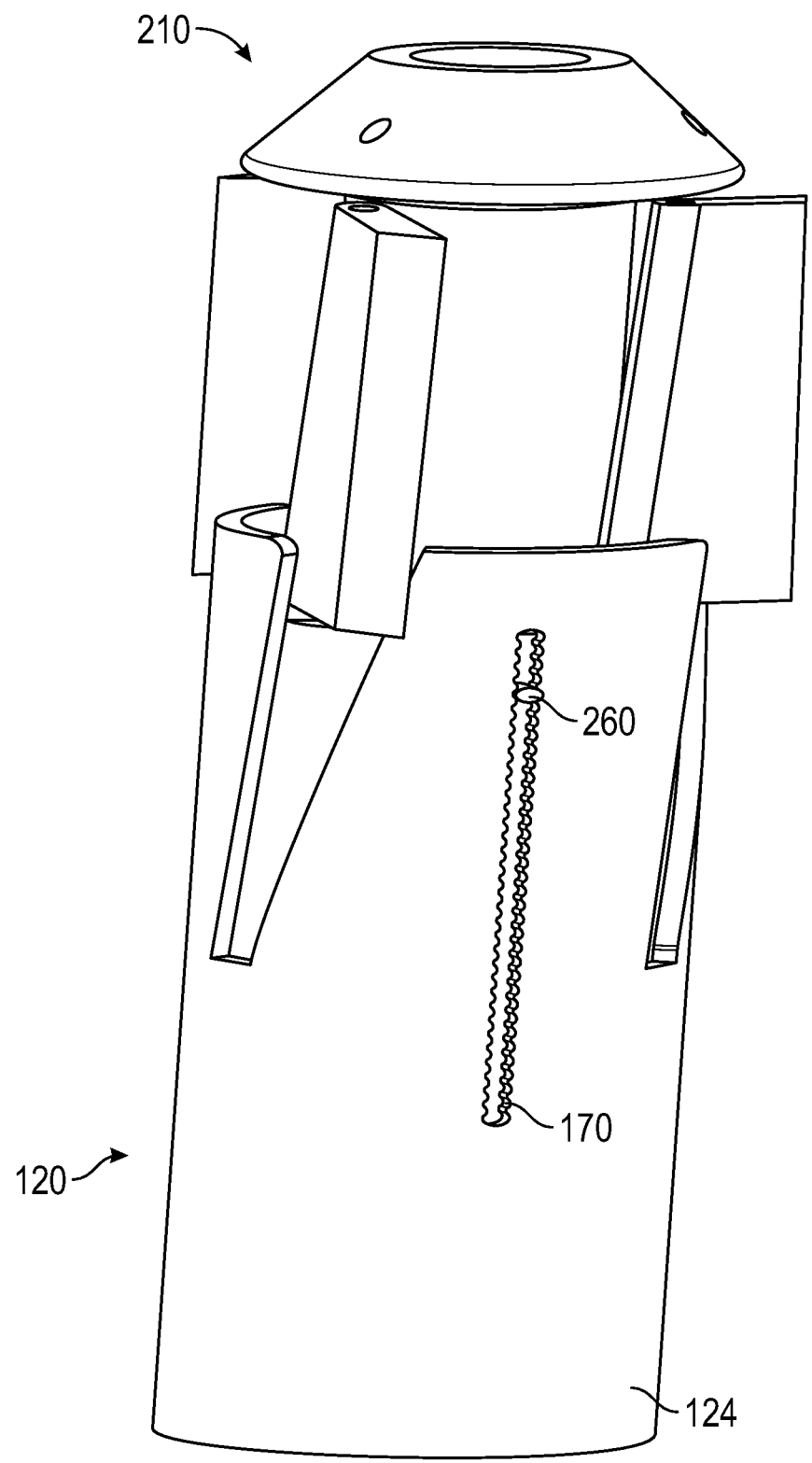
FIG. 6D shows another section side view of the elongated cutter guide and mandrel of FIG. 1A.

In addition, the elongated aperture/slot 170 further includes a series of detents/catches 176 located along the opposing longitudinal sides of the elongated aperture/slot 170. As shown by FIGS. 6B and 6C, the detents/catches 176 releasably lock or otherwise releasably hold the longitudinal position of the elongated cutter guide 120 and cylindrical mandrel 210 relative to one another and. more particularly hold the longitudinal position of the elongated cutter guide 120 and cylindrical mandrel 210 relative to one another in a series of incremental (stepped) positions relative to one another. In such regards, the anti-rotation mechanism may also similarly be a releasable locking/retaining mechanism. As the tubular body 124 of the elongated cutter guide 120 is moved proximally/distally relative to the cylindrical mandrel 210, the position of the pin 260 may change within the aperture/slot 170 from a first releasably fixed position to a second releasably fixed position. The detents/catches 176 and/or the pin 260 may resiliently (elastically) deform to enable the pin 260 to travel within aperture/slot 170.

In addition, the tubular body 124 of the elongated cutter guide 120 may include indicia 180, such as numbers or letters. The indicia 180 may represent the various cutter diameters which are available with the medical device 100/cutting end effector (expandable cutting head) 110. As shown, as the tubular body 124 of the elongated cutter guide 120 is moved distally relative to the cutter assembly 200/cylindrical mandrel 210, as shown in FIG. 6B to FIG. 6C, the cutting diameter is indicated has having changed from 10.5 mm to 13.5 mm. In such regards, the anti-rotation mechanism and a releasable locking/retaining mechanism may also be considered a positional feedback/indicator mechanism for the set diameter of the cutting blades 300.

Figure 7:
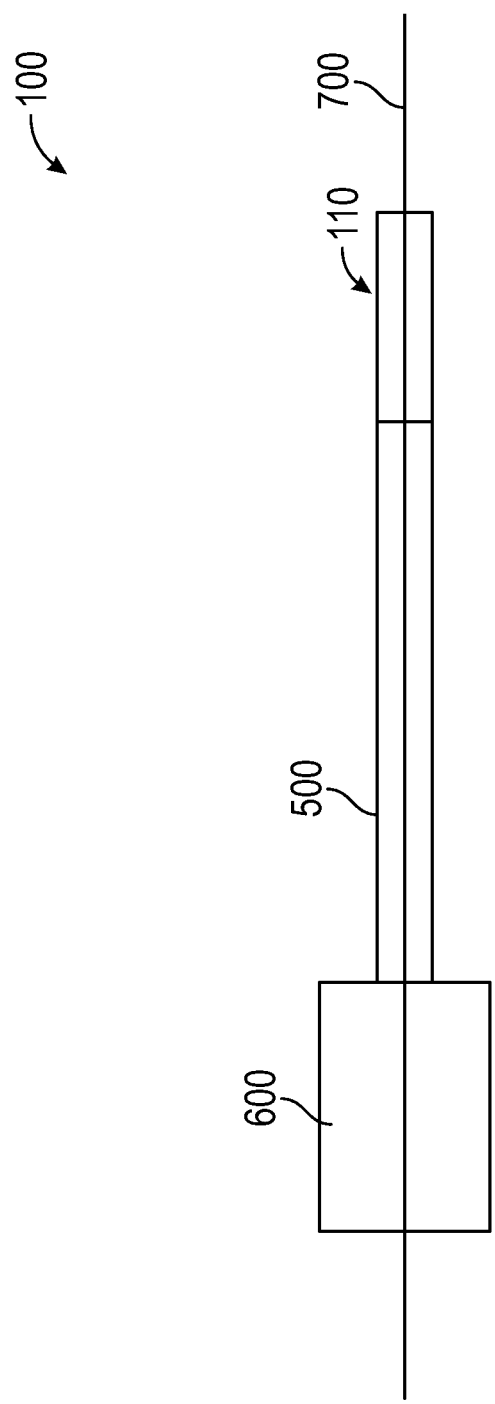
FIG. 7 shows the medical device of FIG. 1A further including additional components.

As shown in FIG. 7, the cutting end effector (expandable cutting head) 110 may be coupled to a flexible drill shaft 500, and more particularly the mandrel 210 may be directly rotateably coupled to the flexible drill shaft 500 with the elongated cutter guide 120 overlying the coupling, which is coupled to a rotary device (drill) 600, through which a guide wire 700 may be extended.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, fifths, tenths, etc. As a non-limiting example, quarters, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 configurations refers to groups having 1, 2, or 3 configurations. Similarly, a group having 1-5 configurations refers to groups having 1, 2, 3, 4, or 5 configurations, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

LISTING OF REFERENCE CHARACTERS 100 medical device
110 cutting end effector/cutter head
120 elongated outer cutter guide
124 circular tubular body
128 cylindrical sidewall
132 inner diameter
134 inner circular (cylindrical) passage
136 distal end
138 distal end opening of passage
142 elongated sidewall aperture
144 section of sidewall trailing cutter
146 section of sidewall leading cutter
148 longitudinal aperture trailing edge
149 distal end of aperture trailing edge
150 longitudinal aperture leading edge
156 proximal end of aperture
158 distal end of aperture
160 distal end opening of aperture
170 elongated aperture/slot
176 detent/catch
180 indicia
200 cutter assembly
210 cylindrical mandrel
212 proximal cylindrical section
214 distal cylindrical section
216 conical distal end section
218 center passage
220 proximal end of the distal end cap
222 face of end cap
223 cutter blades
224 cylindrical surface of distal cylindrical section
226 shoulder region of proximal cylindrical section
228 annular face of proximal cylindrical section
228a face segment of annular face
228b face segment of annular face
230 mounting connector/member of proximal cylindrical section
232 portion of cylindrical mandrel (mounting tab)
236 shoulder region of distal end cap
238 annular face of distal end cap
240 distal mounting connector/member (axle)
242 through-bore
250 annular recess
260 pin
300 elongated cutter
302 cutter blade 306 cutter blade proximal end
308 cutter blade distal end
310 cutter blade leading face
312 cutter blade trailing face
314 bevel
316 leading engagement edge
320 tissue cutting edge
322 taper angle
324 outermost cutting point of cutter blade
330 mounting/connector member
332 proximal mounting/connector member (axle)
334 distal mounting/connector member (bore)
336 central longitudinal axis of axle (pin)
340 elongated cutter pivot axis
350 elongated cutter/cutter blade axle angle
352 blade angle vertex
360 rake angle
400 anti-rotation mechanism/releasable locking/retaining mechanism
500 drill shaft
600 rotary device (drill)
700 guide wire

What is claimed is:

1. A medical device comprising:
a rotatable cutter head having a center longitudinal rotation axis;
the rotatable cutter head comprising a mandrel and a plurality of elongated cutters disposed on the mandrel;
each of the elongated cutters rotatable about a cutter rotation axis, respectively, wherein rotation of each of the elongated cutters about the cutter rotation axis changes a cutting diameter of the rotatable cutter head;
each cutter rotation axis having a length which simultaneously extends both longitudinally along the center longitudinal rotation axis and circumferentially around the center longitudinal rotation axis;
each cutter rotation axis parallel with a first imaginary plane, respectively, which is at an angle with a second imaginary plane which is parallel to the center longitudinal axis, respectively;
wherein the mandrel comprises a proximal cylindrical section, a distal cylindrical section and a distal end section;
wherein the distal cylindrical section is arranged distal of the proximal cylindrical section, and the distal end section is arranged distal of the distal cylindrical section;
wherein the distal cylindrical section has an outer diameter smaller than an outer diameter of the proximal cylindrical section and the distal end section such that an annular recess is formed between the proximal cylindrical section and the distal end section; and
wherein each of the elongated cutters is disposed in the annular recess.

2. The medical device of claim 1, wherein:
the distal end section of the mandrel is conically shaped and/or has a plurality of cutting blades.

3. The medical device of claim 1, wherein:
each of the elongated cutters is rotatable about the cutter rotation axis via an axle rotatable in a bore, respectively.

4. The medical device of claim 3, wherein:
each of the elongated cutters comprises the axle; and
each of the bores is disposed in the mandrel.

5. The medical device of claim 4, wherein:
the mandrel comprises a proximal cylindrical section, a distal cylindrical section and a distal end section;
wherein the distal cylindrical section is arranged distal of the proximal cylindrical section, and the distal end section is arranged distal of the distal cylindrical section;
wherein the distal cylindrical section has an outer diameter smaller than an outer diameter of the proximal cylindrical section and the distal end section such that an annular recess is formed between the proximal cylindrical section and the distal end section;
wherein each of the elongated cutters is disposed in the annular recess; and
wherein each of the bores is disposed in a portion of the mandrel which is part of the proximal cylindrical section and/or the distal cylindrical section.

6. The medical device of claim 5, wherein:
the portion of the mandrel which is part of the proximal cylindrical section and/or the distal cylindrical section of the mandrel comprises a mounting tab.

7. The medical device of claim 6, wherein:
the mounting tab is disposed adjacent a shoulder region of the proximal cylindrical section.

8. The medical device of claim 1, wherein:
each of the elongated cutters is rotatable about the cutter rotation axis via a bore rotatable about an axle, respectively.

9. The medical device of claim 8, wherein:
each of the elongated cutters comprises the bore; and
each of the axles extends from the mandrel and into each of the bores.

10. The medical device of claim 9, wherein:
the mandrel comprises a proximal cylindrical section, a distal cylindrical section and a distal end section;
wherein the distal cylindrical section is arranged distal of the proximal cylindrical section, and the distal end section is arranged distal of the distal cylindrical section;
wherein the distal cylindrical section has an outer diameter smaller than an outer diameter of the proximal cylindrical section and the distal end section such that an annular recess is formed between the proximal cylindrical section and the distal end section;
wherein each of the elongated cutters is disposed in the annular recess; and
wherein each of the axles extends from a bore formed in the distal end section of the mandrel.

11. The medical device of claim 1, wherein:
the rotatable cutter head further comprises an elongated cutter guide, the elongated cutter guide having a tubular body which mechanically engages with the elongated cutters; and
wherein each of the elongated cutters is rotatable about the cutter rotation axis by movement of the tubular body along the longitudinal rotation axis relative to the elongated cutters.

12. The medical device of claim 11, wherein:
the tubular body and the elongated cutters are arranged such that distal movement of the tubular body along the longitudinal rotation axis relative to the elongated cutters increases the cutting diameter of the rotatable cutter head; and
the tubular body and the elongated cutters are arranged such that proximal movement of the tubular body along the longitudinal rotation axis relative to the elongated cutters decreases the cutting diameter of the rotatable cutter head.

13. The medical device of claim 11, wherein:

the tubular body comprises a plurality of cutter guide slots; and wherein each one of the elongated cutters occupies one of the cutter guide slots.

14. The medical device of claim 13, wherein:

each of the cutter guide slots are defined by opposing edges of the tubular body;

wherein the opposing edges defining each cutter guide slot comprise a leading edge which leads the elongated cutter occupying the cutter guide slot in a direction of rotational cutting of the rotatable cutter head, and a trailing edge which trails the elongated cutter occupying the cutter guide slot in a direction of rotational cutting of the rotatable cutter head;

wherein the leading edge of the tubular body defining each cutter guide slot mechanically engages with the elongated cutter occupying the cutter guide slot to increase the cutting diameter of the of the rotatable cutter head; and wherein the training edge of the tubular body defining each cutter guide slot mechanically engages with the elongated cutter occupying the cutter guide slot to decrease the cutting diameter of the of the rotatable cutter head.

15. The medical device of claim 1, wherein:

each of the elongated cutters comprises an elongated, planar cutter blade, respectively; and each of the elongated, planar cutter blades tapers from a proximal end to a distal end at a taper angle.

16. The medical device of claim 15, wherein:

each of the elongated cutter blades has a leading face and a trailing face relative to a cutting direction of the rotatable cutter head; and wherein the trailing face of each of the elongated cutter blades has a bevel.

17. The medical device of claim 1, wherein:

the mandrel has a through-passage which extends along the longitudinal rotation axis.

18. A medical device comprising:

a rotatable cutter head having a center longitudinal rotation axis;

the rotatable cutter head comprising a mandrel and a plurality of elongated cutters disposed on the mandrel;

each of the elongated cutters rotatable about a cutter rotation axis, respectively, wherein rotation of each of the elongated cutters about the cutter rotation axis changes a cutting diameter of the rotatable cutter head;

each cutter rotation axis having a length which simultaneously extends both longitudinally along the center longitudinal rotation axis and circumferentially around the center longitudinal rotation axis;

each elongated cutter comprising a cutter blade having a proximal end and a distal end;

the cutter rotation axis of each elongated cutter is spaced at a radial distance from the longitudinal axis which changes 1.5 mm or less from the proximal end to the distal end of the cutter blade;

wherein the rotatable cutter head further comprises an elongated cutter guide, the elongated cutter guide having a tubular body which mechanically engages with the elongated cutters; and wherein each of the elongated cutters is rotatable about the cutter rotation axis by movement of the tubular body along the longitudinal rotation axis relative to the elongated cutters.

19. A medical device comprising:

a rotatable cutter head having a center longitudinal rotation axis;

the rotatable cutter head comprising a mandrel and a plurality of elongated cutters disposed on the mandrel;

each of the elongated cutters rotatable about a cutter rotation axis, respectively, wherein rotation of each of the elongated cutters about the cutter rotation axis changes a cutting diameter of the rotatable cutter head;

each cutter rotation axis having a length which simultaneously extends both longitudinally along the center longitudinal rotation axis and circumferentially around the center longitudinal rotation axis;

each the cutter rotation axis is spaced at a radial distance from the longitudinal axis; and each cutter rotation axis extends circumferentially around the center longitudinal rotation axis in a range of 1% to 15% of a full rotation around the center longitudinal rotation axis;

wherein the rotatable cutter head further comprises an elongated cutter guide, the elongated cutter guide having a tubular body which mechanically engages with the elongated cutters; and wherein each of the elongated cutters is rotatable about the cutter rotation axis by movement of the tubular body along the longitudinal rotation axis relative to the elongated cutters.

20. A medical device comprising:

a rotatable cutter head having a center longitudinal rotation axis;

the rotatable cutter head comprising a mandrel and a plurality of elongated cutters disposed on the mandrel;

each of the elongated cutters rotatable about a cutter rotation axis, respectively, wherein rotation of each of the elongated cutters about the cutter rotation axis changes a cutting diameter of the rotatable cutter head;

each cutter rotation axis having a length which simultaneously extends both longitudinally along the center longitudinal rotation axis and circumferentially around the center longitudinal rotation axis;

each cutter rotation axis parallel with a first imaginary plane, respectively, which is at an angle with a second imaginary plane which is parallel to the center longitudinal axis, respectively;

wherein the rotatable cutter head further comprises an elongated cutter guide, the elongated cutter guide having a tubular body which mechanically engages with the elongated cutters; and wherein each of the elongated cutters is rotatable about the cutter rotation axis by movement of the tubular body along the longitudinal rotation axis relative to the elongated cutters.

21. The medical device of claim 20, wherein:

the mandrel comprises a proximal cylindrical section, a distal cylindrical section and a distal end section;

wherein the distal cylindrical section is arranged distal of the proximal cylindrical section, and the distal end section is arranged distal of the distal cylindrical section;

wherein the distal cylindrical section has an outer diameter smaller than an outer diameter of the proximal cylindrical section and the distal end section such that an annular recess is formed between the proximal cylindrical section and the distal end section; and wherein each of the elongated cutters is disposed in the annular recess.

22. The medical device of claim 21, wherein:

the distal end section of the mandrel is conically shaped and/or has a plurality of cutting blades.

23. The medical device of claim 20, wherein:
each of the elongated cutters is rotatable about the cutter rotation axis via an axle rotatable in a bore, respectively.

24. The medical device of claim 23, wherein:
each of the elongated cutters comprises the axle; and
each of the bores is disposed in the mandrel.

25. The medical device of claim 24, wherein:
the mandrel comprises a proximal cylindrical section, a distal cylindrical section and a distal end section;
wherein the distal cylindrical section is arranged distal of the proximal cylindrical section, and the distal end section is arranged distal of the distal cylindrical section;
wherein the distal cylindrical section has an outer diameter smaller than an outer diameter of the proximal cylindrical section and the distal end section such that an annular recess is formed between the proximal cylindrical section and the distal end section;
wherein each of the elongated cutters is disposed in the annular recess; and
wherein each of the bores is disposed in a portion of the mandrel which is part of the proximal cylindrical section and/or the distal cylindrical section.

26. The medical device of claim 25, wherein:
the portion of the mandrel which is part of the proximal cylindrical section and/or the distal cylindrical section of the mandrel comprises a mounting tab.

27. The medical device of claim 26, wherein:
the mounting tab is disposed adjacent a shoulder region of the proximal cylindrical section.

28. The medical device of claim 20, wherein:
each of the elongated cutters is rotatable about the cutter rotation axis via a bore rotatable about an axle, respectively.

29. The medical device of claim 28, wherein:
each of the elongated cutters comprises the bore; and
each of the axles extends from the mandrel and into each of the bores.

30. The medical device of claim 29, wherein:
the mandrel comprises a proximal cylindrical section, a distal cylindrical section and a distal end section;
wherein the distal cylindrical section is arranged distal of the proximal cylindrical section, and the distal end section is arranged distal of the distal cylindrical section;
wherein the distal cylindrical section has an outer diameter smaller than an outer diameter of the proximal cylindrical section and the distal end section such that an annular recess is formed between the proximal cylindrical section and the distal end section;
wherein each of the elongated cutters is disposed in the annular recess; and
wherein each of the axles extends from a bore formed in the distal end section of the mandrel.

31. The medical device of claim 20, wherein:
the tubular body and the elongated cutters are arranged such that distal movement of the tubular body along the longitudinal rotation axis relative to the elongated cutters increases the cutting diameter of the rotatable cutter head; and
the tubular body and the elongated cutters are arranged such that proximal movement of the tubular body along the longitudinal rotation axis relative to the elongated cutters decreases the cutting diameter of the rotatable cutter head.

32. The medical device of claim 20, wherein:
the tubular body comprises a plurality of cutter guide slots; and
wherein each one of the elongated cutters occupies one of the cutter guide slots.

33. The medical device of claim 32, wherein:
each of the cutter guide slots are defined by opposing edges of the tubular body;
wherein the opposing edges defining each cutter guide slot comprise a leading edge which leads the elongated cutter occupying the cutter guide slot in a direction of rotational cutting of the rotatable cutter head, and a trailing edge which trails the elongated cutter occupying the cutter guide slot in a direction of rotational cutting of the rotatable cutter head;
wherein the leading edge of the tubular body defining each cutter guide slot mechanically engages with the elongated cutter occupying the cutter guide slot to increase the cutting diameter of the of the rotatable cutter head; and
wherein the training edge of the tubular body defining each cutter guide slot mechanically engages with the elongated cutter occupying the cutter guide slot to decrease the cutting diameter of the of the rotatable cutter head.

34. The medical device of claim 20, wherein:
each of the elongated cutters comprises an elongated, planar cutter blade, respectively; and
each of the elongated, planar cutter blades tapers from a proximal end to a distal end at a taper angle.

35. The medical device of claim 34, wherein:
each of the elongated cutter blades has a leading face and a trailing face relative to a cutting direction of the rotatable cutter head; and
wherein the trailing face of each of the elongated cutter blades has a bevel.

36. The medical device of claim 20, wherein:
the mandrel has a through-passage which extends along the longitudinal rotation axis.

* * * * *